(12) United States Patent
Fujibe et al.

(10) Patent No.: US 8,598,288 B2
(45) Date of Patent: Dec. 3, 2013

(54) CATALYST FOR POLYMERIZATION OF NORBORNENE MONOMERS, METHOD FOR PRODUCING NORBORNENE POLYMER, METHOD FOR PRODUCING NORBORNENE COPOLYMER, NORBORNENE POLYMER AND TRANSITION METAL COMPLEX

(71) Applicant: Showa Denko K.K., Tokyo (JP)

(72) Inventors: Satoshi Fujibe, Oita (JP); Nobuyuki Kibino, Oita (JP); Tsuneo Tajima, Oita (JP)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 13/663,475

(22) Filed: Oct. 30, 2012

(65) Prior Publication Data
US 2013/0059993 A1 Mar. 7, 2013

Related U.S. Application Data

(63) Continuation of application No. PCT/JP2011/071060, filed on Sep. 8, 2011.

(30) Foreign Application Priority Data

Sep. 10, 2010 (JP) .................................. 2010-202562
Jul. 5, 2011 (JP) .................................. 2011-149067

(51) Int. Cl.
*C08F 4/26* (2006.01)
*C08F 4/70* (2006.01)
*C08F 10/14* (2006.01)

(52) U.S. Cl.
USPC ........ 526/172; 526/170; 526/169.1; 526/145; 526/135; 526/281; 526/280; 526/139; 526/169; 502/103

(58) Field of Classification Search
USPC .............. 526/172, 161, 169.1, 169, 170, 139, 526/145
See application file for complete search history.

(56) References Cited

U.S. PATENT DOCUMENTS

| | | | |
|---|---|---|---|
| 3,330,815 A | 7/1967 | McKeon et al. | |
| 5,714,556 A * | 2/1998 | Johnson et al. | 526/135 |
| 6,103,920 A * | 8/2000 | Johnson et al. | 556/140 |
| 6,174,975 B1 * | 1/2001 | Johnson et al. | 526/172 |
| 6,197,715 B1 * | 3/2001 | Bansleben et al. | 502/155 |
| 6,309,997 B1 * | 10/2001 | Fujita et al. | 502/167 |
| 6,410,664 B1 * | 6/2002 | Bansleben et al. | 526/141 |
| 7,060,768 B2 * | 6/2006 | Brookhart et al. | 526/161 |
| 7,566,761 B2 * | 7/2009 | Mitani et al. | 526/172 |
| 8,163,860 B2 * | 4/2012 | Kaita et al. | 526/281 |

FOREIGN PATENT DOCUMENTS

| | | |
|---|---|---|
| EP | 0445755 A2 | 9/1991 |
| JP | 3678754 B2 | 5/1999 |
| JP | 2008-31304 | 2/2008 |
| WO | WO 98/30609 A1 | 7/1998 |
| WO | WO 2006/064814 A1 | 6/2006 |

OTHER PUBLICATIONS

International Search Report for corresponding International Application No. PCT/JP2011/071060, Jun. 19, 2012.

(Continued)

*Primary Examiner* — Rip A. Lee
(74) *Attorney, Agent, or Firm* — Ditthavong Mori & Steiner, P.C.

(57) ABSTRACT

A catalyst for a polymerization of norbornene monomers includes a transition metal complex represented by a formula (1). A method for producing a norbornene copolymer includes copolymerizing first norbornene monomers corresponding to a first monomer unit represented by a formula (2) and second norbornene monomers corresponding to a second monomer unit represented by a formula (3) in a presence of the catalyst. The transition metal complex is preferably (π-allyl) {2-[N-(2,6-diisopropylphenyl) iminomethyl]phenolate}palladium, (π-allyl) {2-[N-(2,6-diisopropylphenyl)iminomethyl]-4-fluorophenolate}palladium, (π-allyl)[2-(N-phenyliminomethyl) phenolate]palladium or (π-allyl){2-[N-(2,6-diisopropylphenyl) iminomethyl]-6-methylphenolate}palladium.

(1)

(2)

-continued
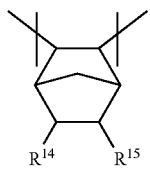
(3)
10 Claims, 8 Drawing Sheets

(56) References Cited

OTHER PUBLICATIONS

Sasabe, Hisahiro et al., "Diastereotopic relationship between planar and central chiralities in the formation of Ru(eta.3-allyl)(CO)(PPh3)(L-L') complexes", Inorganic Chemistry Communications, 6(8), 1140-1143 CODEN: ICCOFP; ISSN: 1387-7003, 2003, XP002669568.

Yang, Hu et al., "(.eta.3-Allyl) palladium complexes of chiral N, O-chelates: preparation, structures, and prospects for selective allylic functionalization", Organometallics, 12(9), 3485-94 CODEN: ORGND7; ISSN: 0276-7333, 1993, XP008148914, p. 3487; examples 4a-d, 5.

Musco, Alfredo et al., "Molecular asymmetry of .pi.-allylic compounds of transition metals. VII. Salicylaldimine derivatives of .pi.-allylic palladium complexes", Gazzetta Chimica Italiana, 104(3-4), 287-95 CODEN: GCITA9; ISSN: 0016-5603, 1974, XP008148908.

Swanton, P. F. et al., "Unusually large PMR coupling constants in .pi.-allylpalladium complexes", Spectroscopy Letters, 5(9), 307-10 CODEN: SPLEBX: ISSN: 0038-7010, 1972, XP008148907.

Reichert, B. E. et al., ".pi.-Allylic palladium Schiff-base complexes", Journal of Organometallic Chemistry, 36(1), C29-C31 CODEN: JORCAI; ISSN: 0022-328X, 1972, XP008148910.

Jung, Il Gu et al., "Polymerization of 5-norbornene-2-methyl acetate catalyzed by air-stable cationic (.eta.3-substituted allyl) palladium complexes of N-heterocyclic carbene", Journal of Organometallic Chemistry 694, 2009, pp. 297-303.

\* cited by examiner

CATALYST FOR POLYMERIZATION OF NORBORNENE MONOMERS, METHOD FOR PRODUCING NORBORNENE POLYMER, METHOD FOR PRODUCING NORBORNENE COPOLYMER, NORBORNENE POLYMER AND TRANSITION METAL COMPLEX

CROSS-REFERENCES TO RELATED APPLICATIONS

The present application is a continuation application of International Application No. PCT/JP2011/071060, filed Sep. 8, 2011, which claims priority under 35 U.S.C. §119 to Japanese Patent Application No. 2010-202562, filed Sep. 10, 2010, and to Japanese Patent Application No. 2011-149067, filed Jul. 5, 2011. The contents of these applications are incorporated herein by reference in their entirety.

BACKGROUND OF THE INVENTION

1. Field of the Invention

The present invention relates to a catalyst for a polymerization of norbornene monomers, a method for producing a norbornene polymer, a method for producing a norbornene copolymer, a norbornene polymer and a transition metal complex.

2. Discussion of the Background

Conventionally, addition polymers of cyclic olefins represented by norbornene polymers have been industrially used in the field of optical films and the like as an organic material being excellent in heat resistance and transparency. There have been various reports that such addition polymers of cyclic olefins can be produced by the addition polymerization of cyclic olefin monomer(s) using a catalyst containing transition metal compounds such as Ti, Zr, Cr, Co, Ni and Pd.

For example, the European Patent Publication No. 0445755 reports that an addition homopolymer of norbornene having the number average molecular weight exceeding 1,000,000 can be produced by polymerizing a norbornene monomer alone by using a transition metal compound of elements belonging to five to ten groups of the periodic table as a main catalyst and methylaluminoxane (MAO) as a cocatalyst.

U.S. Pat. No. 3,330,815 publication discloses addition homopolymers of norbornene monomers containing polar groups and copolymers with norbornene using only dichlorobis(benzonitrile)palladium and allyl palladium chloride dimer as a catalyst.

Japanese Patent No. 3678754 (WO96/37526) and JP-A-2008-31304 publication disclose a method for improving an addition polymerization of a norbornene monomer alone containing polar group or copolymerization with norbornene. Though these methods improved both of polymerization activity and molecular weight of the obtained polymer by using a combination of allyl palladium chloride dimer, silver tetrafluoroborate and silver hexafluorophosphate as a catalyst, they only disclose copolymer having number average molecular weight less than 200,000 in examples and have not succeeded in producing copolymers having number average molecular weight of 200,000 or more which is required for mechanical properties to be developed to a practical level. In Table 1 of JP-A-2008-31304, the number average molecular weight (Mn) entries and the weight average molecular weight (Mw) entries replace each other. It is obvious from that Mw/Mn values should be around 2.5, and it is clear that a copolymer having a number average molecular weight exceeding 200,000 did not exist if data in Table 1 are interpreted properly.

International publication No. WO06/064814 (US 2009/264608) discloses that addition copolymerization of norbornene containing polar group and norbornene can be efficiently performed by using compounds of transition metals belonging to eighth to tenth groups of the periodic table as a main catalyst in combination with a cocatalyst capable of producing a cationic transition metal compound through the reaction with the main catalyst to thereby obtain copolymers having high molecular weight.

As one of the methods to prevent the catalyst deactivation due to the coordinate bonding of norbornene with a transition metal complex, it is possible to extend the distance between the polymerizable carbon-carbon double bonding and a polar group (ester group). For example, "J. Organomet. Chem., 2009, 694, p. 297-303" discloses a case of producing a homopolymer of a norbornene compound wherein a one methylene chain is introduced between the norbornene skeleton and an ester group, having a number average molecular weight of 100,000 or more, by using N-heterocyclic carbene complex.

SUMMARY OF THE INVENTION

According to one aspect of the present invention, a catalyst for a polymerization of norbornene monomers includes a transition metal complex represented by a formula (1).

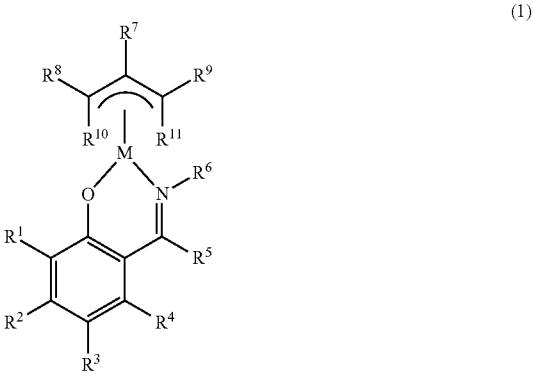

M represents one transition metal belonging to Group 8, Group 9 or Group 10 of the Periodic Table of the Elements issued in 1991.

Each of $R^1$, $R^2$, $R^3$ and $R^4$ independently represents a hydrogen atom, a substituted or unsubstituted hydrocarbon group having 1 to 20 carbon atoms, a halogen atom, an alkoxy group, an aryloxy group, a silyl group having 1 to 20 carbon atoms, a siloxy group containing a hydrocarbon group having 1 to 20 carbon atoms, a nitro group, a cyano group, an amide group containing a hydrocarbon group having 1 to 10 carbon atoms or a dialkylamino group containing an alkyl group having 1 to 10 carbon atoms, or each of $R^1$, $R^2$, $R^3$ and $R^4$ independently represents a hydrogen atom, a substituted or unsubstituted hydrocarbon group having 1 to 20 carbon atoms, a halogen atom, an alkoxy group, an aryloxy group, a silyl group having 1 to 20 carbon atoms, a siloxy group containing a hydrocarbon group having 1 to 20 carbon atoms, a nitro group, a cyano group, an amide group containing a hydrocarbon group having 1 to 10 carbon atoms or dialkylamino group containing an alkyl group having 1 to 10 carbon atoms, and at least two of $R^1$, $R^2$, $R^3$ and $R^4$ bond to each other to form a ring structure.

$R^5$ represents a hydrogen atom or a hydrocarbon group having 1 to 20 carbon atoms.

$R^6$ represents a hydrocarbon group having 1 to 20 carbon atoms.

Each of $R^7$, $R^8$, $R^9$, $R^{10}$ and $R^{11}$ independently represents a hydrogen atom, a halogen atom or a hydrocarbon group having 1 to 20 carbon atoms, or each of $R^7$, $R^8$, $R^9$, $R^{10}$ and $R^{11}$ independently represents a hydrogen atom, a halogen atom or a hydrocarbon group having 1 to 20 carbon atoms, and at least two of $R^7$, $R^8$, $R^9$, $R^{10}$ and $R^{11}$ bond to each other to form a ring structure.

According to another aspect of the present invention, a method for producing a norbornene polymer includes homopolymerizing norbornene monomers in a presence of the catalyst.

According to further aspect of the present invention, a method for producing a norbornene copolymer includes copolymerizing norbornene monomers in a presence of the catalyst.

According to further aspect of the present invention, a method for producing a norbornene copolymer includes copolymerizing norbornene monomers and vinyl monomers in a presence of the catalyst.

According to further aspect of the present invention, a method for producing a norbornene copolymer includes copolymerizing first norbornene monomers corresponding to a first monomer unit represented by a formula (2) and second norbornene monomers corresponding to a second monomer unit represented by a formula (3) in a presence of the catalyst as claimed in claim 1 to form the norbornene copolymer including the first monomer unit and the second monomer unit.

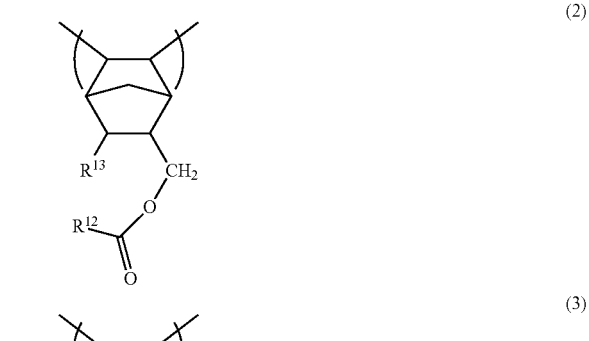

$R^{12}$ represents an alkyl group having 1 to 10 carbon atoms, and each of $R^{12}$, $R^{14}$ and $R^{15}$ independently represents a hydrogen atom or an alkyl group having 1 to 10 carbon atoms.

According to further aspect of the present invention, a norbornene polymer essentially consists of a monomer unit represented by a formula (2). The norbornene polymer has a number average molecular weight (Mn) of 200,000 to 1,000,000.

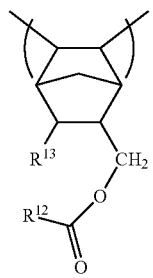

$R^{12}$ represents an alkyl group having 1 to 10 carbon atoms, and $R^{13}$ represents a hydrogen atom or an alkyl group having 1 to 10 carbon atoms.

According to further aspect of the present invention, a transition metal complex is shown by (π-allyl){2-[N-(2,6-diisopropylphenyl)iminomethyl]phenolate}palladium.

According to further aspect of the present invention, a transition metal complex is shown by (π-allyl){2-[N-(2,6-diisopropylphenyl)iminomethyl]-4-fluorophenolate}palladium.

According to further aspect of the present invention, a transition metal complex is shown by (π-allyl)[2-(N-phenyliminomethyl)phenolate]palladium.

According to further aspect of the present invention, a transition metal complex is shown by (π-allyl){2-[N-(2,6-diisopropylphenyl)iminomethyl]-6-methylphenolate}palladium.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings.

DESCRIPTION OF THE EMBODIMENTS

Figure 1:
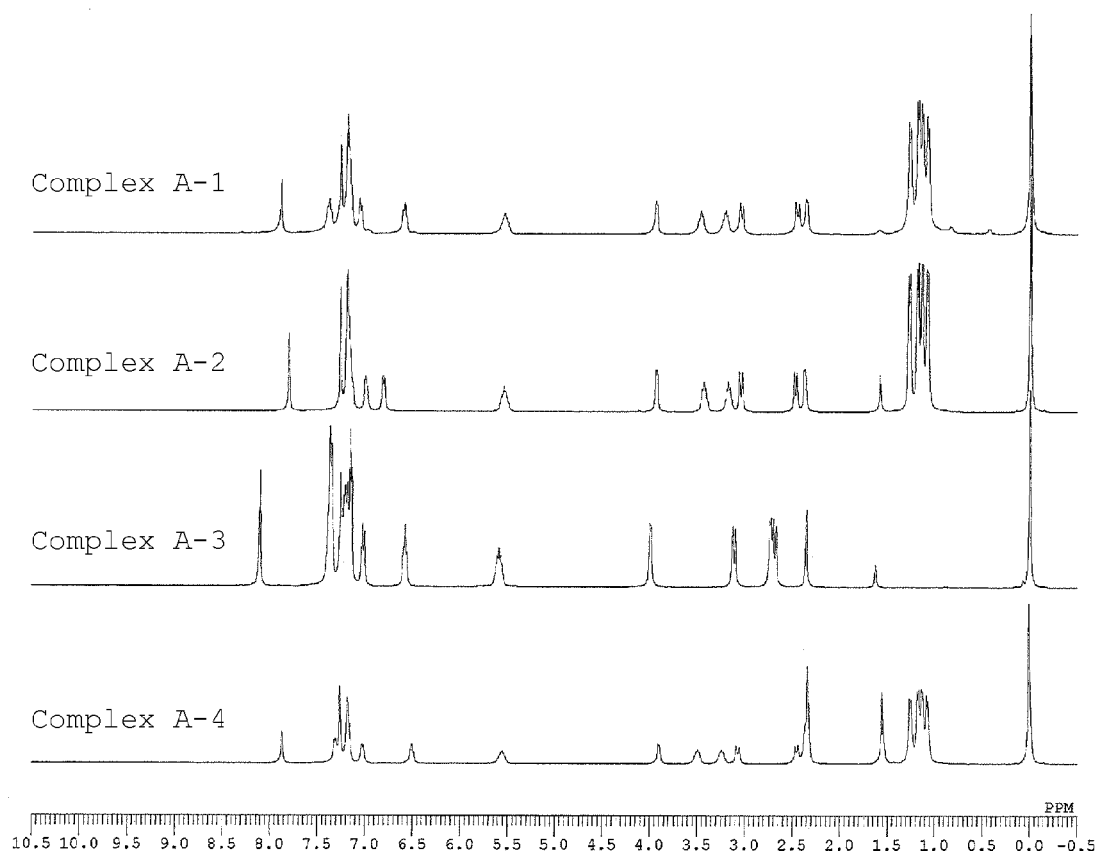
FIG. 1 is a $^1$H-NMR spectrum of the complex obtained in Examples 1 to 4.

The embodiments of the present invention relate to the catalyst for the polymerization of norbornene monomers in [1] to [6], the method for producing norbornene copolymer in [7] to [10], the norbornene copolymer in [11] and the palladium complex in [12] to [15] as described below.

[1] A catalyst for the polymerization of norbornene monomers, containing transition metal complex (A) represented by formula (1)

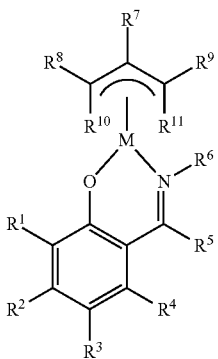

(1)

(in the formula, M represents one transition metal selected from the elements belonging to eight, nine or ten group of the periodic table for 1991, and $R^1$, $R^2$, $R^3$ and $R^4$ independently represent a hydrogen atom; a hydrocarbon group having 1 to 20 carbon atoms which may contain a substituent; a halogen atom; alkoxy group; aryloxy group, silyl group having 1 to 20 carbon atoms; siloxy group containing a hydrocarbon group having 1 to 20 carbon atoms; nitro group; cyano group; an amide group containing a hydrocarbon group having 1 to 10 carbon atoms; or dialkylamino group containing an alkyl group having 1 to 10 carbon atoms; $R^1$, $R^2$, $R^3$ and $R^4$ may bond to each other to form a ring structure; $R^5$ represents a hydrogen atom or a hydrocarbon group having 1 to 20 carbon atoms; $R^6$ represents a hydrocarbon group having 1 to 20 carbon atoms; $R^7$, $R^8$, $R^9$, $R^{10}$ and $R^{11}$ represent independently from each other a hydrogen atom, a halogen atom or a hydrocarbon group having 1 to 20 carbon atoms; and $R^7$, $R^8$, $R^9$, $R^{10}$ and $R^{11}$ may bond to each other to form a ring structure.)

[2] The catalyst for the polymerization of norbornene monomers as described in [1] above, wherein M represents palladium (Pd) or nickel (Ni); $R^5$ represents a hydrogen atom; $R^6$ represents a phenyl group which may contain a substituent; and all of $R^7$, $R^8$, $R^9$, $R^{10}$ and $R^{11}$ represent a hydrogen atom in formula (1).

[3] The catalyst for the polymerization of norbornene monomers as described in [2] above, wherein M represents palladium; $R^1$ represents a hydrogen atom or a methyl group; both of $R^2$ and $R^4$ represent a hydrogen atom; $R^3$ represents a hydrogen atom or fluorine atom; and $R^6$ represents a phenyl group or a 2,6-diisopropylphenyl group in formula (1).

[4] The catalyst for the polymerization of norbornene monomers as described in any one of [1] to [3] above, comprising cocatalyst (B) as being an ionic compound which can generate a cationic transition metal compound by reacting with transition metal complex (A) and a phosphine ligand (C).

[5] The catalyst for the polymerization of norbornene monomers as described in [4] above, wherein cocatalyst (B) is trityltetrakis(pentafluorophenyl)borate or N,N-dimethylaniliniumtetrakis(pentafluorophenyl)borate.

[6] The catalyst for the polymerization of norbornene monomers as described in [4] above, wherein phosphine ligand (C) is tricyclohexylphosphine, tri-t-butylphosphine or tri-isopropylphosphine.

[7] A method for producing norbornene (co)polymers comprising homopolymerization of norbornene monomers alone or copolymerization of norbornene monomers in the presence of the catalyst as described in any one of [1] to [6] above.

[8] A method for producing norbornene copolymers comprising copolymerization of norbornene monomers and other vinyl monomers in the presence of the catalyst as described in any one of [1] to [6] above.

[9] A method for producing norbornene copolymers containing monomer units represented by formulae (2) and (3),

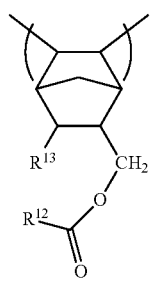

(2)

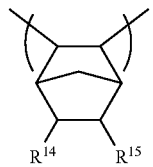

(3)

(in the formula, $R^{12}$ represents an alkyl group having 1 to 10 carbon atoms; and $R^{13}$, $R^{14}$ and $R^{15}$ independently represent a hydrogen atom or an alkyl group having 1 to 10 carbon atoms), comprising polymerization of norbornene monomers corresponding to the monomer unit represented by formulae (2) and (3) in the presence of the catalyst as described in any one of [1] to [6] above.

[10] The method for producing norbornene copolymers as described in [9] above, wherein the copolymers comprise a monomer unit represented by formulae (2) and (3) only.

[11] Norbornene polymers comprising a monomer unit represented by formula (2) as described in [9] above only and having a number average molecular weight (Mn) of 200,000 to 1,000,000.

[12] (π-allyl){2-[N-(2,6-diisopropylphenyl)iminomethyl]phenolate}palladium.

[13] (π-allyl){2-[N-(2,6-diisopropylphenyl)iminomethyl]-4-fluorophenolate}palladium.

[14] (π-allyl)[2-(N-phenyliminomethyl)phenolate]palladium.

[15] (π-allyl){2-[N-(2,6-diisopropylphenyl)iminomethyl]-6-methylphenolate}palladium.

[16] A method for producing norbornene (co)polymers by precipitation polymerization using a solvent which dissolves monomers and does not dissolve polymers of the monomers, wherein the solvent of the precipitation polymerization contains aliphatic carboxylic acid ester.

[17] The method for producing norbornene copolymers as described in [16] above, wherein the norbornene (co)polymers contain a monomer unit represented by formulae (2) and (3)

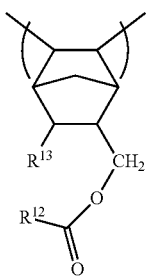

(2)

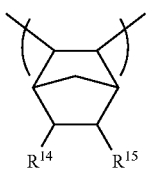

(3)

(in the formula, $R^{12}$ represents an alkyl group having 1 to 10 carbon atoms; and $R^{13}$, $R^{14}$ and $R^{15}$ independently represent a hydrogen atom or an alkyl group having 1 to 10 carbon atoms).

[18] The method for producing norbornene copolymers as described in [17] above, wherein the copolymers comprise a monomer unit represented by formula (2) and formula (3) only.

[19] The method for producing norbornene copolymers as described in any one of [16] to [18] above, wherein the solvent of the precipitation polymerization contains 60% by volume or more of aliphatic carboxylic acid ester.

[20] The method for producing norbornene copolymers as described in any one of [16] to [19] above, wherein the aliphatic carboxylic acid ester is ester of aliphatic carboxylic acid having 1 to 5 carbon atoms and alcohol.

[21] The method for producing norbornene copolymers as described in any one of [16] to [20] above, wherein the aliphatic carboxylic acid ester is ester of carboxylic acid and alcohol having 1 to 5 carbon atoms.

[22] The method for producing norbornene copolymers as described in any one of [16] to [19] above, wherein the aliphatic carboxylic acid ester is at least one member of ethyl acetate, (n-propyl)acetate, isopropyl acetate and (n-butyl)acetate.

[23] The method for producing norbornene copolymers as described in any one of [16] to [18] above, wherein the solvent of the precipitation polymerization contains toluene and 60 percent volume or more of ethyl acetate.

The embodiments of the present invention enable efficiently producing high-molecular weight addition copolymers of norbornene and norbornene monomers containing polar groups. The norbornene copolymer obtained by the embodiments of the present invention has excellent properties such as transparency, heat resistance, low water absorption and electric insulating property, and can be used for many applications such as optics application, application in medical treatment, electronic material application, packaging material application and structural material application.

Specifically, the copolymers can be used for optical molded products such as lenses and polarizing films; electric insulating materials for films, carrier tapes, film capacitors, flexible printed circuit boards, etc.; and medical containers such as press-through packages, infusion bags and chemical vials; food-packaging molded product such as plastic wraps and trays; casings for electric appliances; automobile interior parts such as an inner panel; building materials for a carport, glazing and the like; etc.

The embodiments will now be described with reference to the accompanying drawings.

[Catalyst for Polymerization of Norbornene Monomers]

The catalyst for the polymerization of norbornene monomers of the embodiment of the present invention comprises transition metal complex (A) as an essential component and cocatalyst (B) as being an ionic compound which can generate a cationic transition metal compound by reacting with transition metal complex (A) (hereinafter may be abbreviated as "cocatalyst (B)") and a phosphine ligand (C) as an optional component.

Transition Metal Complex (A)

The transition metal complex (A) of the embodiment of the present invention is characterized in comprising a transition metal having π-allyl ligand selected from the elements belonging to eight, nine or ten group of the periodic table for 1991 and a bidentate salicylaldimine ligand.

The transition metal complex (A) as a component for the catalyst for polymerizing norbornene monomers of the embodiment of the present is a transition metal complex represented by formula (1).

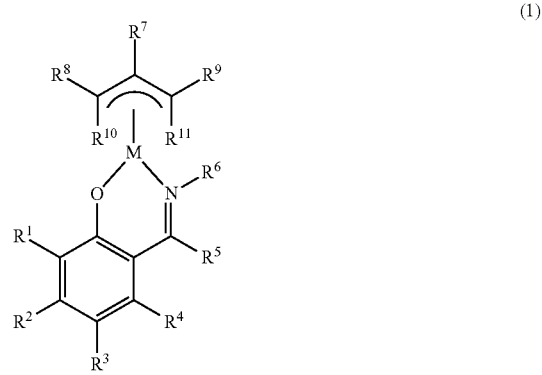

(1)

M in formula (1) represents one transition metal selected from the elements belonging to eight, nine or ten group of the periodic table for 1991. Specific examples include iron (Fe), cobalt (Co), nickel (Ni), ruthenium (Ru), rhodium (Rh), palladium (Pd) and platinum (Pt). Among these, preferred elements are cobalt, nickel, palladium and platinum from the viewpoint of the stability of the complex and ease of synthesis, and using nickel or palladium is more preferable.

$R^1$, $R^2$, $R^3$ and $R^4$ in formula (1) independently represent a hydrogen atom; a hydrocarbon group having 1 to 20 carbon atoms which may contain a substituent; a halogen atom; alkoxy group; aryloxy group, silyl group having 1 to 20 carbon atoms; siloxy group containing a hydrocarbon group having 1 to 20 carbon atoms; nitro group; cyano group; an amide group containing a hydrocarbon group having 1 to 10 carbon atoms; or dialkylamino group containing an alkyl group having 1 to 10 carbon atoms; and $R^1$, $R^2$, $R^3$ and $R^4$ may bond to each other to form a ring structure.

Specific examples of the hydrocarbon group having 1 to 20 carbon atoms which may contain a substituent include an alkyl group having 1 to 20 carbon atoms, which contains a linear or branched chain, such as a methyl group, ethyl group, n-propyl group, isopropyl group, n-butyl group, t-butyl group, isobutyl group, octyl group, 2-ethylhexyl group and 2-methoxyethyl group; a cycloalkyl group having 3 to 20 carbon atoms, such as a cyclopentyl group, cyclohexyl group, 3-methoxycyclohexyl group, 4-methylcyclohexyl group and adamantyl group; an aryl group, an alkylaryl group or aralkyl group having 6 to 20 carbon atoms such as a phenyl group, naphthyl group, anthracenyl group, tolyl group, xylyl group, benzyl group and 4-fluorophenyl group. Examples of a halogen atom include a chlorine atom and a fluorine atom. As an alkoxy group, an alkoxy group having 1 to 20 carbon atoms are preferable and specific examples include methoxy group, ethoxy group, isopropoxy group and sec-butoxy group. Examples of aryloxy group include phenoxy group and benzyloxy group. Examples of silyl group containing hydrocarbon group having 1 to 20 carbon atoms include trimethylsilyl group, triethylsilyl group, t-butyldimethylsilyl group and t-butyldiphenylsilyl group; and examples of siloxy group containing hydrocarbon group having 1 to 20 carbon atoms include trimethylsiloxy group and triethylsiloxy group. Other examples include nitro group, cyano group, amide group containing hydrocarbon group containing 1 to 10 carbon atoms, and dialkylamino group containing alkyl group having 1 to 10 carbon atoms. Among these, preferred are a hydrogen atom, an alkyl group having 1 to 6 carbon atoms and a halogen atom from the viewpoint of ease of synthesizing a complex, and a hydrogen atom, an alkyl group having 1 to 3 carbon atoms and a fluorine atom are particularly preferable.

$R^5$ in formula (1) represents a hydrogen atom or a hydrocarbon group having 1 to 20 carbon atoms. Specific examples include a hydrogen atom; an alkyl group having 1 to 20 carbon atoms, which contains a linear or branched chain, such as a methyl group, ethyl group, n-propyl group, isopropyl group, n-butyl group, t-butyl group, isobutyl group, octyl group and 2-ethylhexyl group; a cycloalkyl group having 3 to 20 carbon atoms such as a cyclopentyl group, cyclohexyl group and 4-methylcyclohexyl group; and an aryl group, an alkylaryl group or aralkyl group having 6 to 20 carbon atoms such as a phenyl group, tolyl group, xylyl group and benzyl group. Among these, preferred are a hydrogen atom and an alkyl group having 1 to 6 carbon atoms from the viewpoint of ease of synthesizing a complex, and a hydrogen atom is particularly preferable.

$R^6$ in formula (1) represents a hydrocarbon group having 1 to 20 carbon atoms. Specific examples include an alkyl group having 1 to 20 carbon atoms, which contains a linear or branched chain, such as a methyl group, ethyl group, n-propyl group, isopropyl group, n-butyl group, t-butyl group, isobutyl group, octyl group and 2-ethylhexyl group; a cycloalkyl group having 3 to 20 carbon atoms such as a cyclopentyl group, cyclohexyl group and 4-methylcyclohexyl group; and an aryl group, an alkylaryl group or aralkyl group having 6 to 20 carbon atoms such as a phenyl group, tolyl group, xylyl group, 2,6-diisopropylphenyl group and benzyl group. Among these, preferred are an aryl group and an alkylaryl group having 6 to 20 carbon atoms from the viewpoint of ease of synthesizing a complex and stability of a complex, and a phenyl group and 2,6-diisopropylphenyl group are particularly preferable.

$R^7$, $R^8$, $R^9$, $R^{10}$ and $R^{11}$ in formula (1) independently represent a hydrogen atom, a halogen atom or a hydrocarbon group having 1 to 20 carbon atoms, and $R^7$, $R^8$, $R^9$, $R^{10}$ and $R^{11}$ may form a ring structure by bonding to each other. Specific examples include a hydrogen atom; a halogen atom such as a fluorine atom, chlorine atom and bromine atom; an alkyl group having 1 to 20 carbon atoms, which contains a linear or branched chain, such as a methyl group, ethyl group, n-propyl group, isopropyl group, n-butyl group, t-butyl group, isobutyl group, octyl group and 2-ethylhexyl group; an alkenyl group having 2 to 20 carbon atoms, which contains a linear or branched chain, such as an ethenyl group and 2-propenyl group; and an aryl group, an alkylaryl group or aralkyl group having 6 to 20 carbon atoms such as a phenyl group, tolyl group and xylyl group. Among these, preferred are a hydrogen atom, an alkyl group having 1 to 6 carbon atoms and an aryl group having 6 to 10 carbon atoms from the viewpoint of ease of synthesizing a complex, and a hydrogen atom and a methyl group are particularly preferable.

Specific examples of the transition metal complex (A) represented by formula (1) are given below but the transition metal complex (A) is not limited thereto. In the specific examples described below, "M" has the same meaning as "M" in formula (1). Also, Me, Et, t-Bu and Ph respectively represent a methyl group, an ethyl group, a t-butyl group and a phenyl group.

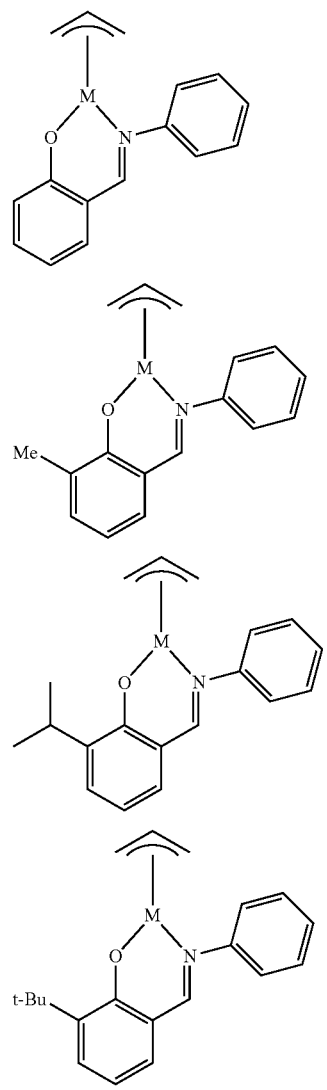

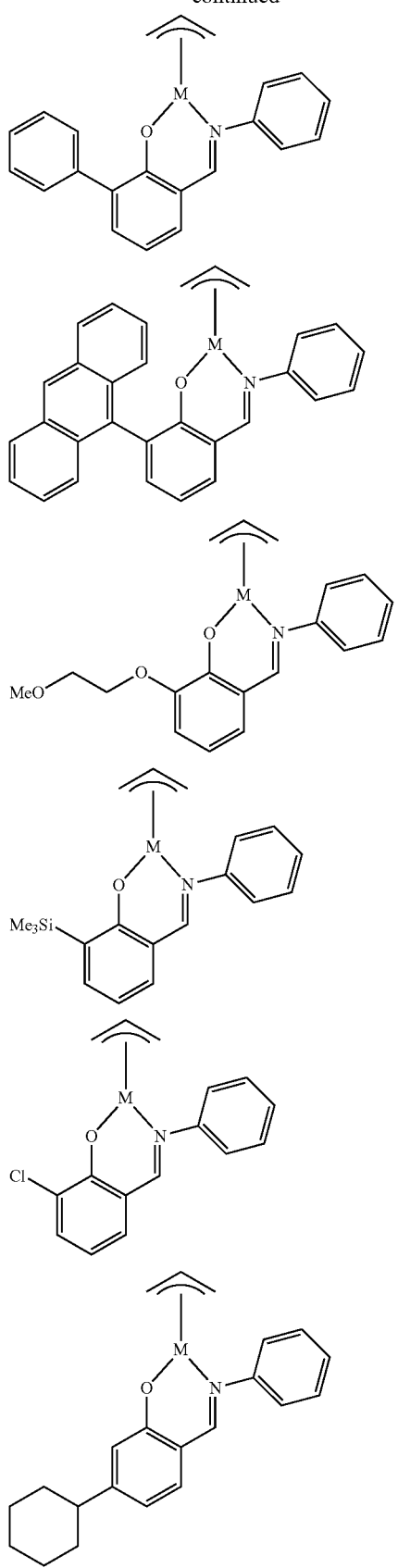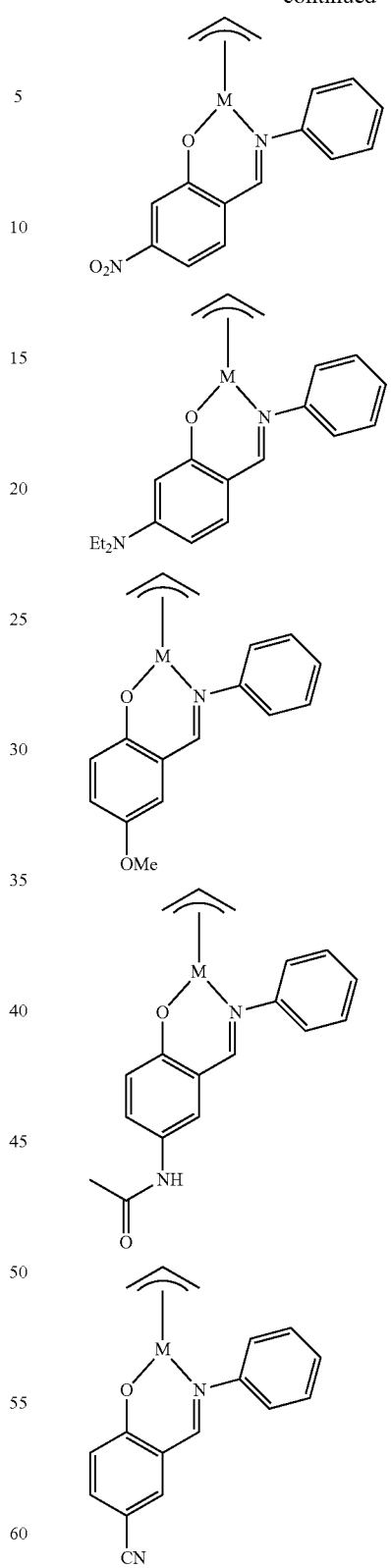

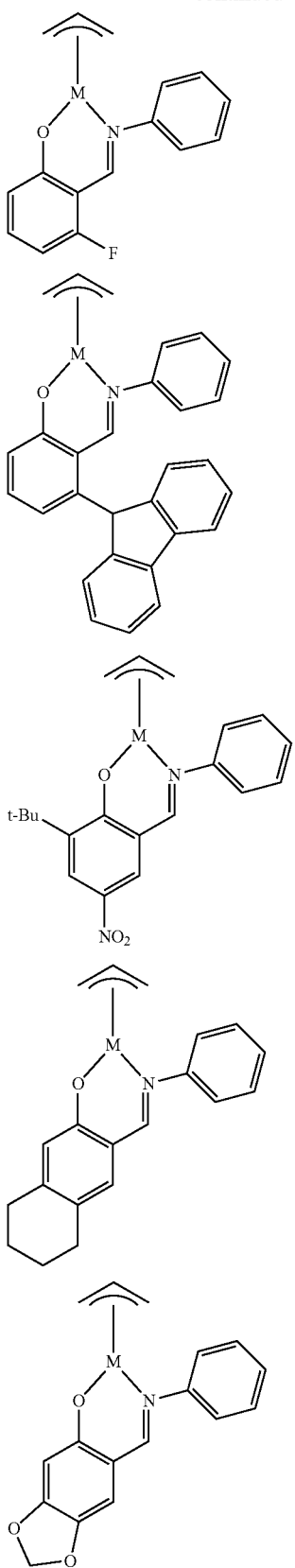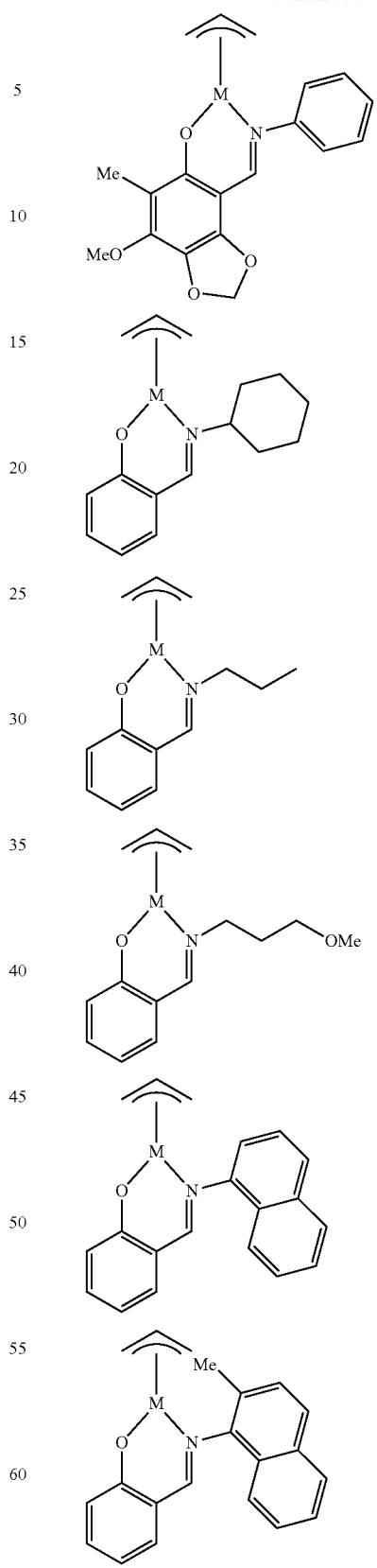

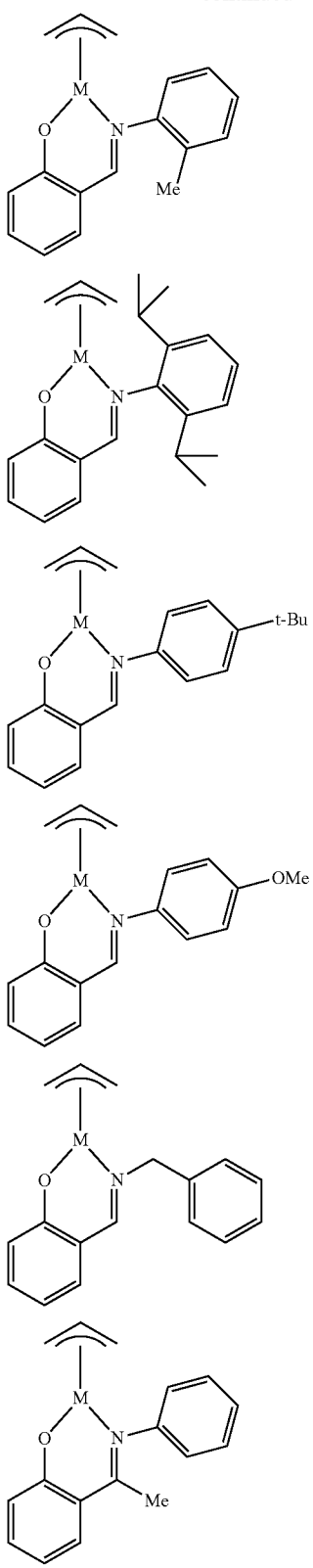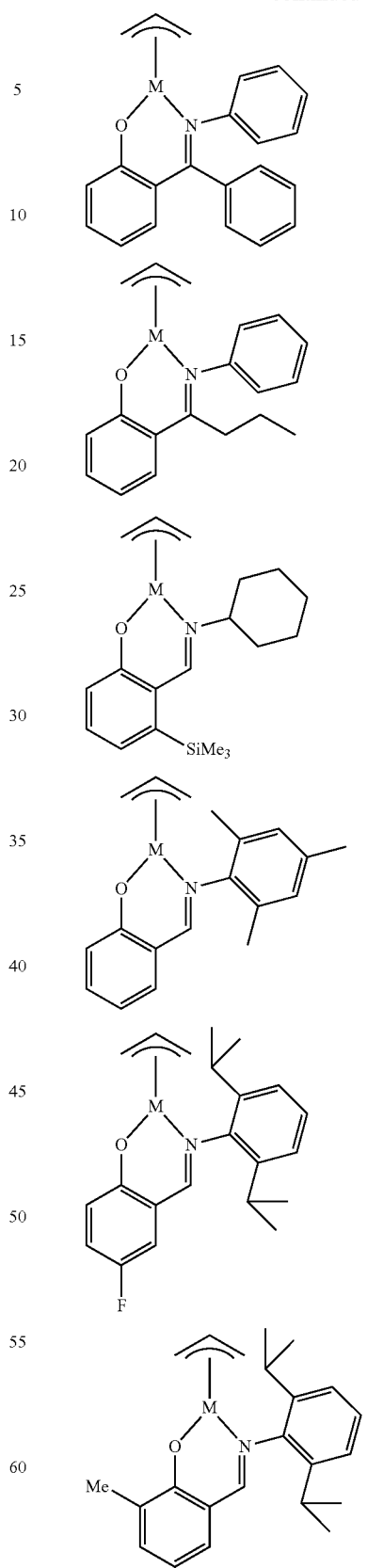

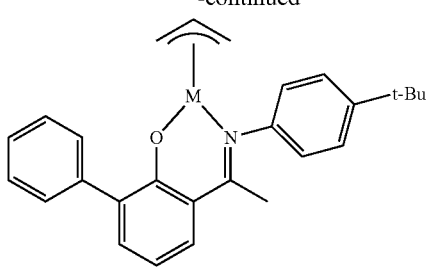
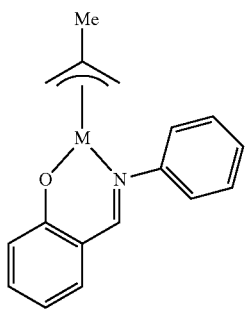
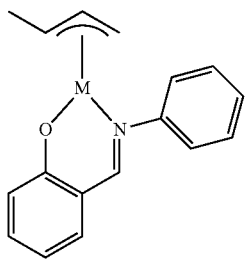
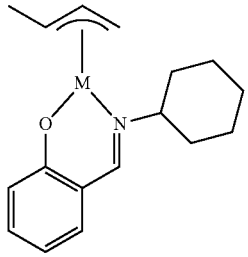
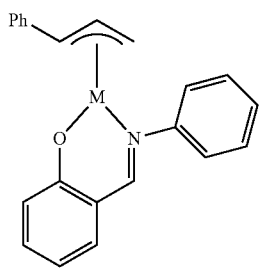
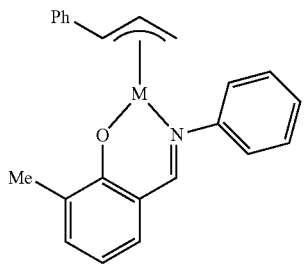
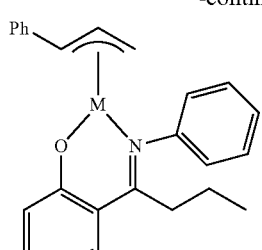
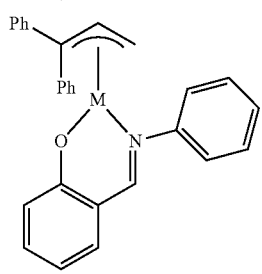
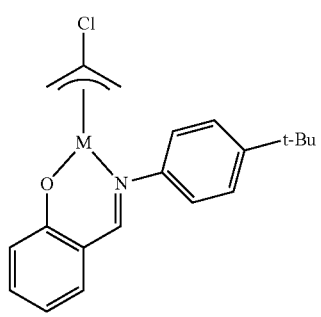
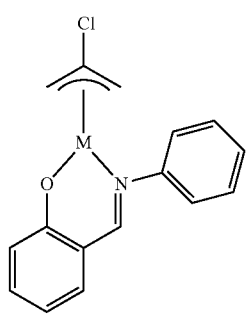
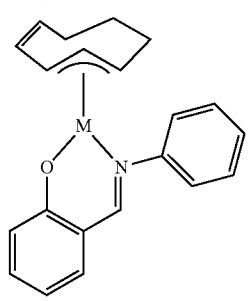
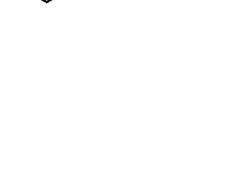

-continued

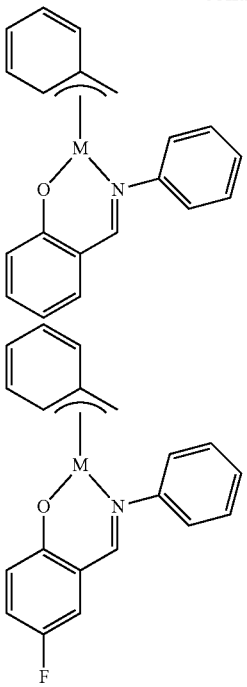

Among these, (π-allyl){2-[N-(2,6-diisopropylphenyl)iminomethyl]phenolate}palladium, (π-allyl){2-[N-(2,6-diisopropylphenyl)iminomethyl]-4-fluorophenolate}palladium, (π-allyl)[2-(N-phenyliminomethyl)phenolate]palladium and (π-allyl){2-[N-(2,6-diisopropylphenyl)iminomethyl]-6-methylphenolate}palladium are preferable in the embodiment of the present invention.

Next, the method for producing the transition metal complex of the embodiment of the present invention in a case where M is palladium is to be described below. The transition metal complex of the embodiment of the present invention can be produced similarly when M is transition metal other than palladium.

The transition metal complex (A) of the embodiment of the present invention can be produced by the ligand exchange reaction of a (π-allyl)palladium(II) compound as a precursor and a salicylaldimine compound of the formula below

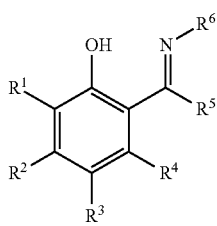

($R^1$, $R^2$, $R^3$, $R^4$, $R^5$ and $R^6$ in the formula have the same meanings as in formula (1)). An example of the specific production method can be exemplified by the method disclosed by J. Organomet. Chem., 1974, 81, 227-246.

There is no particular limitation on a (π-allyl)palladium(II) compound as long as the compound contains a ligand capable of carrying out a ligand exchange reaction with a salicylaldimine compound. For example, di(π-allyl)di(μ-chloro)dipalladium and (π-allyl)(acetylacetonato)palladium are preferable.

Specific examples of a salicylaldimine compound used for producing transition metal complex (A) are given below but the salicylaldimine compound is not limited thereto.

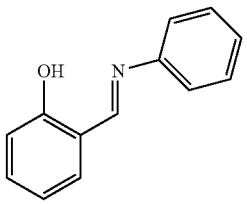

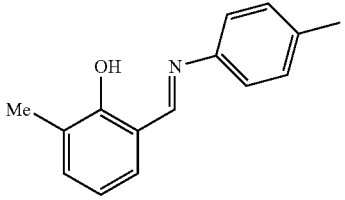

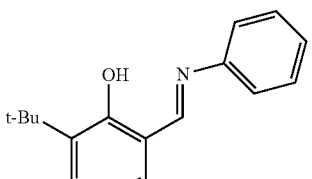

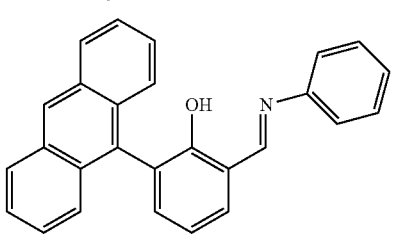

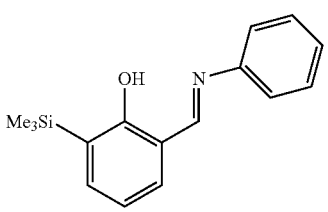

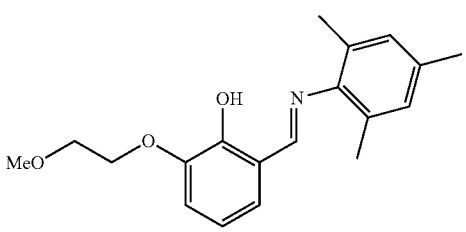

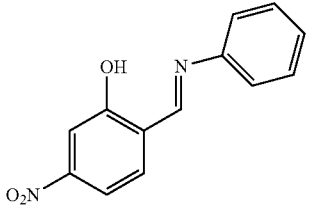

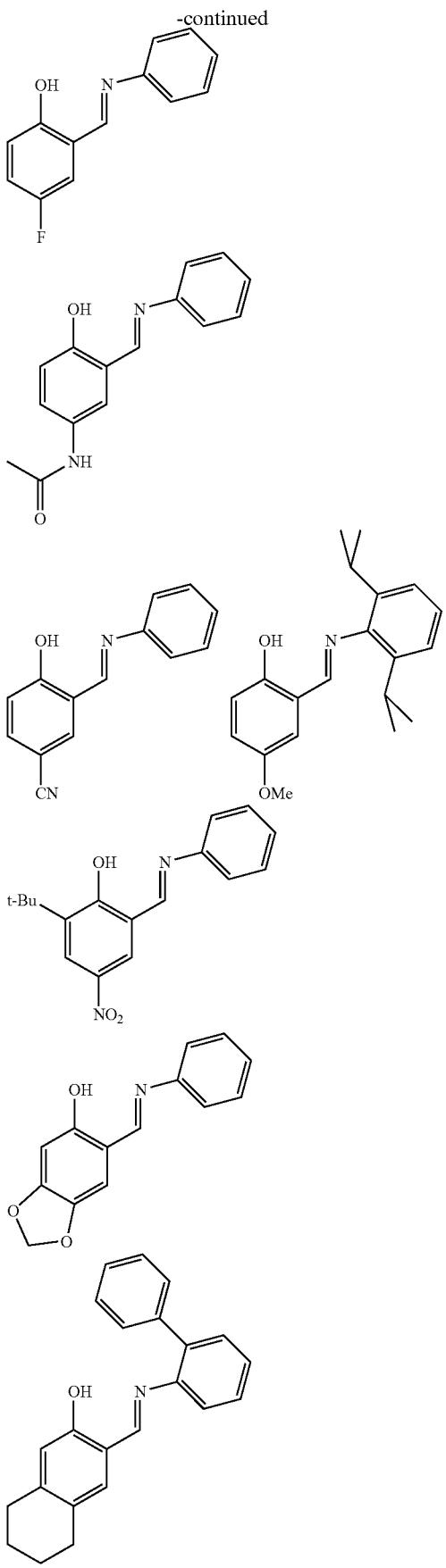
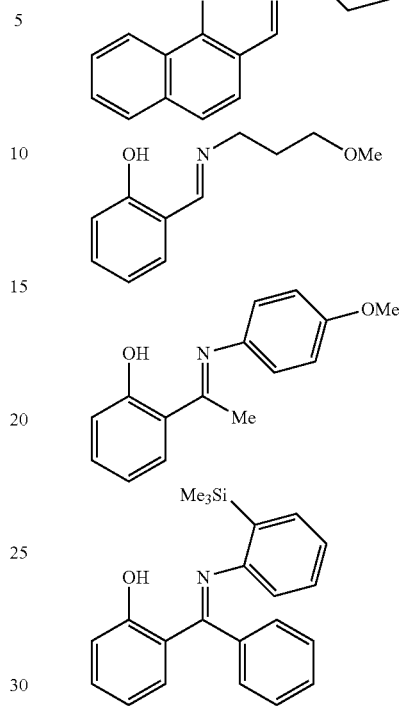

For such a salicylaldimine compound, commercially available ones can be used as they are. A compound produced by the method described by Organometallics, 1998, 17, p. 3149-3151 or Organometallics, 1998, 17, p. 3460-3465 can also be used.

The above-mentioned ligand exchange reaction can be performed by adding a salicylaldimine compound or a salicylaldimine compound with base added as needed to a (π-allyl)palladium(II) compound as a precursor dissolved in a solvent followed by stirring at a predetermined temperature for a predetermined time.

There is no particular limitation on a solvent used in the ligand exchange reaction as long as the solvent is not reactive with each substrate, and examples include aliphatic hydrocarbon such as pentane, hexane and heptane; alicyclic hydrocarbon such as cyclohexane; aromatic hydrocarbon such as benzene, toluene and xylene; halogenated hydrocarbon such as dichloromethane, chloroform and chlorobenzene; nitrogen-containing hydrocarbon such as nitromethane, nitrobenzene and acetonitrile; and ether such as diethyl ether, dioxane and tetrahydrofuran. Two or more of these solvents may be used in mixture. It is preferable to use a solvent subjected to dehydration and deaeration.

There is no particular limitation on the usage of a solvent as long as it does not significantly delay the reaction, and the usage can be appropriately determined depending on the solubility of the (π-allyl)palladium(II) compound as a precursor and the like. Generally, 1 to 100 g of a solvent is used based on 1 g of (π-allyl)palladium(II) compound as a precursor.

There is no particular limitation on the polymerization temperature but the temperature is generally from −100° C. to 150° C., preferably from −50° C. to 120° C. If the temperature is lower than −100° C., it lowers the reaction rate. If the temperature is higher than 150° C., it results in decomposition of the generated complex in some cases. The reaction rate can be controlled by selecting the reaction temperature within the above-mentioned range.

The reaction time is not particularly limited and, for example, from one minute to 50 hours. Also, it is preferable to conduct reaction under inert gas atmosphere such as nitrogen gas.

After the completion of the reaction, the target transition metal complex (A) can be isolated by performing general isolation/purification operation. Specifically, the target transition metal complex (A) is isolated by removing the salt generated in the reaction by centrifugation and filtration followed by recrystallization of the salt.

Whether the product obtained by the reaction is the target transition metal complex (A) can be confirmed by NMR spectrum, mass spectrum, X-ray crystallographic analysis and the like.

The thus obtained transition metal complex (A) is useful as a catalyst component for the polymerization of norbornene monomers.

While the catalyst for the polymerization of norbornene monomers of the embodiment of the present invention may be a compound containing at least one member of transition metal complex (A), it is preferable that the catalyst further contains cocatalyst (B) as being an ionic compound which can generate a cationic transition metal compound by reacting with transition metal complex (A) and a phosphine ligand (C), which enables exhibition of enhanced catalyst activity.

Cocatalyst (B)

Examples of cocatalyst (B) capable of producing a cationic transition metal compound through the reaction with the transition metal complex (A) used in the embodiment of the present invention include an ionic compound combining non-coordinating anions and cations.

Examples of non-coordinating anions include quaternary anions of the Group 13 element in the periodic table for 1991. Specific examples include tetra(phenyl)borate, tetra(fluorophenyl)borate, tetrakis(difluorophenyl)borate, tetrakis(trifluorophenyl)borate, tetrakis(tetrafluorophenyl)borate, tetrakis(pentafluorophenyl)borate, tetrakis(tetrafluoromethyl phenyl)borate, tetrakis[3,5-di(trifluoromethyl)phenyl]borate, tetra(triyl)borate, tetra(xylyl)borate, triphenyl(pentafluorophenyl)borate, [tris(pentafluorophenyl)phenyl]borate and tridecahydride-7,8-dicarbaundeca-borate.

Examples of the above-mentioned cation include carbonium cation, oxonium cation, ammonium cation, phosphonium cation, cycloheptyltrienyl cation and ferrocenium cation having transition metal.

Specific examples of the carbonium cation include trisubstituted carbonium cation such as triphenylcarbonium cation and trisubstituted phenylcarbonium cation. Specific examples of trisubstituted phenylcarbonium cation include tri(methylphenyl)carbonium cation and tri(dimethylphenyl)carbonium cation.

Specific examples of the oxonium cation include alkyloxonium cation such as hydroxonium cation and methyloxonium cation, dialkyloxonium cation such as dimethyloxonium cation, and trialkyloxonium cation such as trimethyloxonium cation and triethyloxonium cation.

Specific examples of the ammonium cation include trialkylammonium cation such as trimethylammonium cation, triethylammonium cation, tripropylammonium cation, tributylammonium cation, tri(n-butyl)ammonium cation; and N,N-dialkylanilinium cation such as N,N-diethylanilinium cation, N,N-2,4,6-pentamethylanilinium cation; and dialkylammonium cation such as di(isopropyl)ammonium cation and dicyclohexylammonium cation.

Specific examples of the phosphonium cation include triarylphosphonium cation such as triphenylphosphonium cation, tri(methylphenyl)phosphonium cation and tri(dimethylphenyl)phosphonium cation.

Specific examples of the ferrocenium cation include dialkylferrocenium cation such as ferrocenium cation, 1,1-dimethylferrocenium cation and 1,1-diethylferrocenium cation.

Preferred examples of cocatalyst (B) are trityl tetrakis(pentafluorophenyl)borate, triphenylcarboniumtetra(fluorophenyl)borate, N,N-dimethylanilinium tetrakis(pentafluorophenyl)borate, trityltetrakis[3,5-di(trifluoromethyl)phenyl]borate, N,N-dimethylanilinium tetrakis[3,5-di(trifluoromethyl)phenyl]borate and 1,1'-dimethylferrocenium tetrakis(pentafluorophenyl)borate.

Phosphine Ligand (C)

Phosphine ligand (C) used in the embodiment of the present invention is a trivalent phosphorus compound composed of three substituents selected independently from a hydrogen atom, an alkyl group or an aryl group. Specific examples include trialkylphosphine such as trimethylphosphine, triethylphosphine, triisopropylphosphine and tri-t-butylphosphine; and tricycloalkylphosphine such as tricyclopentylphosphine, tricyclohexylphosphine; and triarylphosphine such as triphenylphosphine. Among these, tricyclohexylphosphine, tri-t-butylphosphine and triisopropylphosphine are preferable from the viewpoint of enhancing the catalytic activity.

In the embodiment of the present invention, a catalyst using a complex represented by formula (1) as transition metal complex (A), wherein $R^1$, $R^2$, $R^3$ and $R^4$ represent a hydrogen atom, a methyl group or a halogen atom; $R^5$ represents a hydrogen atom; $R^6$ represents an alkyl-substituted phenyl group, and all of $R^7$, $R^8$, $R^9$, $R^{10}$ and $R^{11}$ represent a hydrogen atom; N,N-dimethylaniliniumtetrakis(pentafluorophenyl)borate $\{[Ph(Me)_2NH][B(C_6F_5)_4]\}$ or trityltetrakis(pentafluorophenyl)borate $\{[Ph_3C][B(C_6F_5)_4]\}$ as cocatalyst (B); and triisopropylphosphine or tri-t-butylphosphine as phosphine ligand (C) is one of the preferable embodiments of the catalyst capable of producing norbornene polymers with high catalytic activity.

Also, a catalyst using a complex represented by formula (1) as transition metal complex (A), wherein $R^1$ and $R^3$ represent a methyl group or a fluorine atom; $R^2$, $R^4$ and $R^5$ represent a hydrogen atom; $R^6$ represents a phenyl group or a 2,6-diisopropylphenyl group; and all of $R^7$, $R^8$, $R^9$, $R^{10}$ and $R^{11}$ represent a hydrogen atom; N,N-dimethylaniliniumtetrakis(pentafluorophenyl)borate $\{[Ph(Me)_2NH][B(C_6F_5)_4]\}$ as cocatalyst (B); and triisopropylphosphine as phosphine ligand (C) is the most preferable embodiment of the catalyst capable of producing norbornene polymers with high catalytic activity.

The use ratio of transition metal complex (A) and cocatalyst (B) in the method of the embodiment of the present invention varies depending on conditions and cannot be uniformly defined, however, the ratio of (A)/(B) (molar ratio) is generally from 1/0.1 to 1/100, preferably from 1/0.5 to 1/50, still more preferably from 1/1 to 1/10.

The use ratio of transition metal complex (A) and phosphine ligand (C) in the method of the embodiment of the present invention varies depending on conditions and cannot be uniformly defined, however, the ratio of (A)/(C) (molar ratio) is generally from 1/0.1 to 1/2, preferably from 1/0.5 to 1/1.8, still more preferably from 1/1 to 1/1.5.

There is no particular limitation on the temperature at which the catalyst components are placed in contact with each other but the temperature is generally from −100° C. to 150° C., preferably from −50° C. to 120° C. If the temperature is lower than −100° C., it lowers the reaction rate between each other of the components. If the temperature is higher than 150° C., it incurs decomposition of each of the components, thereby lowering the catalytic activity. By selecting the contact temperature within the above-mentioned range, the polymerization rate, the molecular weight of the generated polymer and the like can be controlled when the catalyst is used for polymerization.

Each of the catalyst components may be mixed in the presence of a solvent. Though there is no particular limitation on a solvent which can be used, preferred are those which do not have reactivity with each of the catalyst components and are produced at an industrial scale and easily-available. Specific examples of a solvent include aliphatic hydrocarbon such as pentane, hexane and heptane; alicyclic hydrocarbon such as cyclohexane; aromatic hydrocarbon such as benzene, toluene and xylene; halogenated hydrocarbon such as dichloromethane, chloroform and chlorobenzen; nitrogen-containing hydrocarbon such as nitromethane, nitrobenzene and acetonitrile; and ether such as diethylether, dioxane and tetrahydrofurane. Among these, aliphatic hydrocarbon, aromatic hydrocarbon and halogenated hydrocarbon are preferable. Two or more of these solvents may be used in mixture.

[Method for Producing Norbornene Polymers]

The method for producing norbornene polymers of the embodiment of the present invention is characterized in addition polymerization of norbornene monomers in the presence of the catalyst for the polymerization of the embodiment of the present invention.

The production method of the embodiment of the present invention is one of the following methods: i.e. (i) a method of obtaining addition homopolymers of norbornene monomers by the addition polymerization of one type of norbornene monomer alone, (ii) a method of obtaining addition copolymers of norbornene monomers by the addition copolymerization of two or more types of norbornene monomers, and (iii) a method of obtaining addition copolymers of norbornene monomers by the addition copolymerization of one or more types of norbornene monomers and one or more types of other vinyl monomers which is copolymerizable with norbornene monomers.

Norbornene Monomers

There is no particular limitation on the norbornene monomer used in the embodiment of the present invention as long as it is a compound containing a norbornene ring structure (hereinafter may be simply referred to as "norbornenes"). The compound may contain a polar or nonpolar substituent and may contain a ring structure other than a norbornene ring.

As norbornenes, compounds represented by formula (4) are preferable.

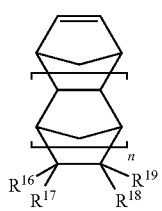

(4)

In the formula, $R^{16}$ to $R^{19}$ each independently represents a hydrogen atom; a halogen atom; a functional group containing a nitrogen atom, an oxygen atom, a sulfur atom, a halogen atom or a silicon atom; and a hydrocarbon group having 1 to 20 carbon atoms which may contain a halogen atom or the above-mentioned functional group. Also, $R^{16}$ to $R^{19}$ may bond to each other to form a ring. n is 0 or 1.

Norbornenes represented by formula (4) can be classified into bicycle[2.2.1]hepto-2-enes in which n is 0 and tetracyclo[6.2.1³,⁶.0²,⁷]dodeca-4-enes in which n is 1. Either of them may be used in the production method of the embodiment of the present invention.

Specific examples of $R^{16}$ to $R^{19}$ in formula (4) include a hydrogen atom; a halogen atom such as a chlorine atom, a bromine atom and a fluorine atom; a functional group containing an oxygen atom such as hydroxyl group, alkoxy group, aryloxy group, carbonyl group, hydroxycarbonyl group, alkoxycarbonyl group and aryloxycarbonyl group; a functional group containing a nitrogen atom such as amino group, alkylamino group, arylamino group, aminocarbonyl group, alkylaminocarbonyl group, arylaminocarbonyl group and cyano group; a functional group containing a sulfur atom such as mercapto group, alkoxythio group and aryloxythio group; and a functional group containing a silicon atom such as silyl group, alkylsilyl group, arylsilyl group, alkoxysilyl group and aryloxysilyl group. Examples also include a hydrocarbon group having 1 to 20 carbon atoms such as alkyl group, alkenyl group and aryl group which may contain these functional groups. Furthermore, $R^{16}$ to $R^{19}$ may bond to each other to form a ring and examples of such a case include an acid anhydride structure, carbonate structure and dithiocarbonate structure.

Specific examples of norbornenes used in the embodiment of the present invention include bicyclo[2.2.1]hept-2-enes, which are unsubstituted or have hydrocarbon group, such as 2-norbornene, 5-methyl-2-norbornene, 5-ethyl-2-norbornene, 5-n-butyl-2-norbornene, 5-n-hexyl-2-norbornene, 5-n-decyl-2-norbornene, 5-cyclohexyl-2-norbornene, 5-ethylidene-2-norbornene, 5-vinyl-2-norbornene, 5-phenyl-2-norbornene, 5-benzyl-2-norbornene, dicyclopentadiene, dihydrodicyclopentadiene, tetracyclo[9.2.1.0²,¹⁰.0³,⁸]tetradeca-3,5,7,12-tetraene, tetracyclo[10.2.1.0²,¹¹.0⁴,⁹]pentadeca-4,6,8,13-tetraene;

tetracyclo[6.2.1.1³,⁶.0²,⁷]dodeca-4-enes, which are unsubstituted or have hydrocarbon group, such as tetracyclo[6.2.1.1³,⁶.0²,⁷]dodeca-4-ene, 9-methyltetracyclo[6.2.1.1³,⁶.0²,⁷]dodeca-4-ene, 9-ethyltetracyclo[6.2.1.1³,⁶.0²,⁷]dodeca-4-ene, 9-n-butyltetracyclo[6.2.1.1³,⁶.0²,⁷]dodeca-4-ene, 9-cyclohexyltetracyclo[6.2.1.1³,⁶.0²,⁷]dodeca-4-ene, 9-ethylidenetetracyclo[6.2.1.1³,⁶.0²,⁷]dodeca-4-ene, 9-vinyltetracyclo[6.2.1.1³,⁶.0²,⁷]dodeca-4-ene and 9-phenyltetracyclo[6.2.1.1³,⁶.0²,⁷]dodeca-4-ene;

bicyclo[2.1.1]hept-2-enes having alkoxycarbonyl group such as methyl 5-norbornene-2-carboxylate, ethyl 5-norbornene-2-carboxylate, n-butyl 5-norbornene-2-carboxylate, methyl 2-methyl-5-norbornene-2-carboxylate, ethyl 2-methyl-5-norbornene-2-carboxylate, n-butyl 2-methyl-5-norbornene-2-carboxylate, methyl 5-norbornene-2,3-dicarboxylate and ethyl 5-norbornene-2,3-dicarboxylate; tetracyclo[6.2.1.1³,⁶.0²,⁷]dodeca-9-enes having alkoxycarbonyl group such as methyl tetracyclo[6.2.1.1³,⁶.0²,⁷]dodeca-9-ene-4-carboxylate, ethyl tetracyclo[6.2.1.1³,⁶.0²,⁷]dodeca-9-ene-4-carboxylate, methyl 4-methyltetracyclo[6.2.1.1³,⁶.0²,⁷]dodeca-9-ene-4-carboxylate, methyl tetracyclo[6.2.1.1³,⁶.0²,⁷]dodeca-9-ene-4,5-dicarboxylate and ethyl tetracyclo[6.2.1.1³,⁶.0²,⁷]dodeca-9-ene-4,5-dicarboxylate;

bicyclo[2.2.1]hept-2-enes having hydroxycarbonyl group such as 5-norbornene-2-carboxylic acid and 5-norbornene-2,3-dicarboxylic acid; tetracyclo[6.2.1.1³,⁶.0²,⁷]dodeca-9-enes having hydroxycarbonyl group such as tetracyclo[6.2.1.1³, ₆.0²,⁷]dodeca-9-ene-4-carboxylic acid and tetracyclo[6.2.1.1³,⁶.0²,⁷]dodeca-9-ene-4,5-dicarboxylic acid;

bicyclo[2.2.1]hept-2-enes having hydroxyl group such as 2-hydroxy-5-norbornene, 2-hydroxymethyl-5-norbornene, 2,2-di(hydroxymethyl)-5-norbornene and 2,3-di(hydroxymethyl)-5-norbornene; tetracyclo[6.2.1.1³,⁶.0²,⁷]dodeca-9-enes having hydroxyl group such as tetracyclo[6.2.1.1³,⁶.0²,⁷]dodeca-9-ene-4-01, tetracyclo[6.2.1.1³,⁶.0²,⁷]dodeca-9-ene-4-methanol and tetracyclo[6.2.1.1³,⁶.0²,⁷]dodeca-9-ene-4,5-dimethanol;

bicyclo[2.2.1]hept-2-enes having acetoxyl group such as 2-acetoxy-5-norbornene, 2-acetoxymethyl-5-norbornene, 2,2-di(acetoxymethyl)-5-norbornene and 2,3-di(acetoxymethyl)-5-norbornene; tetracyclo[6.2.1.1³,⁶.0²,⁷]dodeca-9-enes having acetoxyl group such as 4-acetoxytetracyclo[6.2.1.1³,⁶.0²,⁷]dodeca-9-ene, 4-acetoxymethyltetracyclo[6.2.1.1³,⁶.0²,⁷]dodeca-9-ene, and 4,5-di(acetoxymethyl)tetracyclo[6.2.1.1³,⁶.0²,⁷]dodeca-9-ene;

bicyclo[2.2.1]hept-2-enes having a functional group containing a nitrogen atom such as 5-norbornene-2-carbonitrile and 5-norbornene-2-carboxamide; tetracyclo[6.2.1.1³,⁶.0²,⁷]dodeca-9-enes having a functional group containing a nitrogen atom such as tetracyclo[6.2.1.1³,⁶.0²,⁷]dodeca-9-ene-4-carbonitrile and tetracyclo[6.2.1.1³,⁶.0²,⁷]dodeca-9-ene-4-carboxamide;

bicyclo[2.2.1]hept-2-enes having a halogen atom such as 2-chloro-5-norbornene and 2-fluoro-5-norbornene; tetracyclo[6.2.1.1³,⁶.0²,⁷]dodeca-9-enes having a halogen atom such as 4-chlorotetracyclo[6.2.1.1³,⁶.0²,⁷]dodeca-9-ene and 4-fluorotetracyclo[6.2.1.1³,⁶.0²,⁷]dodeca-9-ene;

bicyclo[2.2.1]hept-2-enes having a functional group containing a silicon atom such as 2-trimethyloxy-5-norbornene, 2-trimethoxysilyl-5-norbornene and 2-tris(trimethoxysilyloxy)silyl-5-norbornene; tetracyclo[6.2.1.1³,⁶.0²,⁷]dodeca-9-enes having a functional group containing a silicon atom such as 4-trimethylsiloxytetracyclo[6.2.1.1³,⁶.0²,⁷]dodeca-9-ene, 4-trimethoxylsilyltetracyclo[6.2.1.1³,⁶.0²,⁷]dodeca-9-ene, 4-tris(trimethoxylsilyloxy)tetracyclo[6.2.1.1³,⁶.0²,⁷]dodeca-9-ene, bicyclo[2.2.1]hept-2-enes having an acid anhydride structure, a carbonate structure and dithiocarbonate structure such as 5-norbornene-2,3-dicarboxylic acid anhydride, 5-norbornene-2,3-carbonate and 5-norbornene-2,3-dithiocarbonate; and tetracyclo[6.2.1.1³,⁶.0²,⁷]dodeca-9-enes having an acid anhydride structure, a carbonate structure and dithiocarbonate structure such as tetracyclo[6.2.1.1³,⁶.0²,⁷]dodeca-9-ene-4,5-dicarboxylic acid anhydride, tetracyclo[6.2.1.1³,⁶.0²,⁷]dodeca-9-ene-4,5-carbonate and tetracyclo[6.2.1.1³,⁶.0²,⁷]dodeca-9-ene-4,5-dithiocarbonate.

These norbornenes may be used singly or in combination of two or more thereof.

Among these norbornenes, it is preferable to use norbornenes corresponding to the monomer unit represented by formulae (2) and (3) in the embodiment of the present invention

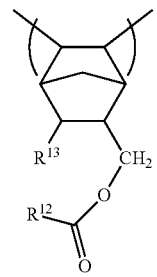

(2)

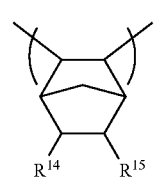

(3)

(in the formula, $R^{12}$ represents an alkyl group having 1 to 10 carbon atoms, and $R^{13}$, $R^{14}$ and $R^{15}$ each independently represent a hydrogen atom or an alkyl group having 1 to 10 carbon atoms).

Alkyl groups having 1 to 10 carbon atoms represented by $R^{12}$ in formula (2) may be linear or branched.

Examples of linear alkyl groups include methyl group, ethyl group, n-propyl group, n-butyl group, n-pentyl group, n-hexyl group, n-octyl group and n-decyl group.

Examples of branched alkyl groups include isopropyl group, isobutyl group, sec-butyl group, neo-pentyl group, isohexyl group, isooctyl group and isodecyl group.

Preferred among them as $R^{12}$ are linear alkyl group having 1 to 3 carbon atoms from an economic standpoint. From the viewpoint of costs for producing a monomer, methyl group is particularly preferable.

$R^{13}$ in formula (2) and $R^{14}$ and $R^{15}$ in formula (3) independently represent for a hydrogen atom or alkyl group having 1 to 10 carbon atoms, and the alkyl group having 3 to 10 carbon atoms may be branched. Examples of these alkyl groups include those similar to the above-mentioned alkyl groups as $R^{12}$. Preferred among them as $R^{13}$, $R^{14}$ and $R^{15}$ is a hydrogen atom from the viewpoint of costs for producing a monomer.

Provided that $R^{13}$ is a hydrogen atom, the norbornene monomer as a material of the monomer unit represented by formula (2) is 2-acetoxymethyl-5-norbornene when $R^{12}$ is an alkyl group having one carbon atom, 2-[(ethylcarbonyloxy)methyl]-5-norbornene when $R^{12}$ is an alkyl group having two carbon atoms, and 2-[(propylcarbonyloxy)methyl]-5-norbornene when $R^{12}$ is an alkyl group having three carbon atoms.

Provided that $R^{14}$ and $R^{15}$ are hydrogen atoms, the norbornenes as a material of the monomer unit represented by formula (3) is norbornene.

In production method of the embodiment of the present invention, polymerization of a norbornene monomer using the above-mentioned transition metal complex (A), cocatalyst (B) and phosphine ligand (C) may be performed by bulk polymerization, suspension polymerization, emulsion polymerization, solution polymerization or precipitation polymerization. When the polymerization is performed in a solvent, it is necessary to use a solvent which will not adversely affect the catalyst activity. Examples of a solvent that can be used include aliphatic hydrocarbon such as pentane, hexane and heptane; alicyclic hydrocarbon such as cyclohexane; aromatic hydrocarbon such as benzene, toluene and xylene;

halogenated hydrocarbon such as dichloromethane, chloroform and chlorobenzen; nitrogen-containing hydrocarbon such as nitromethane, nitrobenzene and acetonitrile; ether such as diethylether, dioxane and tetrahydrofurane; ester such as ethyl acetate, n-propyl acetate and n-butyl acetate; lactone such as δ-valero lactone and γ-butyro lactone; and water. Two or more of these solvents may be used in mixture. When water is used as a solvent, the reaction solution may be made in an emulsified state using anionic, cationic or nonionic surfactants and the like.

Precipitation polymerization is a kind of solvent polymerization, and a solvent capable of dissolving monomers but not capable of dissolving polymers is used. Since polymer is precipitated along with polymerization in the precipitation polymerization, it eliminates the needs of a poor solvent such as methanol used in large quantity for reprecipitation purification, which is advantageous in terms of the production cost.

When the (co)polymer comprising the monomer unit represented by formula (2) and formula (3) of the embodiment of the present invention is produced by precipitation polymerization, aliphatic carboxylic acid ester is preferable as a polymerization solvent which is capable of dissolving monomers but not capable of dissolving the generated polymers. There is no particular limitation on a solvent for precipitation polymerization as long as the solvent contains aliphatic carboxylic acid ester, and the solvent may be a mixed solvent comprising two or more kinds of aliphatic carboxylic acid ester. Also, the polymerization solvent may contain a good solvent of the polymer (such as toluene) and a poor solvent to the extent that the generated polymers would not be dissolved. As a good solvent, a solvent capable of dissolving the catalyst may be used. Further, a solvent capable of dissolving monomers but not capable of dissolving the generated polymers other than aliphatic carboxylic acid ester, e.g. n-hexane, may be used in combination. However, when the ratio of aliphatic carboxylic acid ester lowers, it may degrade handleability in some cases: i.e. the generated polymers may not be completely precipitated or may not be precipitated in the powder form.

The aliphatic carboxylic acid ester is preferably ester of aliphatic carboxylic acid having 1 to 5 carbon atoms and alcohol, more preferably aliphatic carboxylic acid alkyl ester of aliphatic carboxylic acid having 1 to 5 carbon atoms and alcohol having 1 to 5 carbon atoms, and still more preferably ethyl acetate, (n-propyl)acetate, isopropyl acetate and (n-butyl)acetate.

The mixed solvent comprising two or more kinds of aliphatic carboxylic acid ester is preferably a mixed solvent comprising two members arbitrarily selected from ethyl acetate, (n-propyl)acetate, isopropyl acetate and (n-butyl)acetate, and more preferably a mixed solvent of ethyl acetate and (n-propyl)acetate. The mixed solvent of aliphatic carboxylic acid ester and other solvent is preferably a mixed solvent of alkyl ester having 1 to 5 carbon atoms as being aliphatic carboxylic acid ester having 1 to 5 carbon atoms and aromatic hydrocarbon, and more preferably a mixed solvent of ethyl acetate and toluene, and (n-propyl)acetate and toluene.

In the method for producing the (co)polymer of the embodiment of the present invention, in the case where a mixed solvent of two or more kinds of aliphatic carboxylic acid esters is used when precipitation polymerization is carried out, there is no particular limitation on the mixing ratio of each of the aliphatic carboxylic acid esters, and a solvent containing aliphatic carboxylic acid esters at any ratio may be used.

When a mixed solvent of aliphatic carboxylic acid ester and other solvent is used, the ratio of the aliphatic carboxylic acid is preferably 60% by volume or more and more preferably 80% by volume or more. When the ratio of the aliphatic carboxylic acid ester is less than 60% by volume, it makes the precipitation of the generated (co)polymer difficult, thereby decreasing the recovery rate of the polymer in some cases. The ratio of the aliphatic carboxylic acid ester means the ratio to the total amount of all the solvent components including a solvent used for dissolving a catalyst.

In the case where aliphatic hydrocarbon such as hexane, heptane and cyclohexane, which is commonly used in general precipitation polymerization, is used as a solvent when precipitation polymerization is carried out in the method for producing the (co)polymer of the embodiment of the present invention, the precipitation of a polymer occurs simultaneously with the generation of the polymer, and the precipitated polymer adheres to the wall of the reactor and aggregates to thereby generate a block object, which makes it impossible to continue stirring the solvent. Therefore, though such a solvent may be used as a solvent for precipitation polymerization, the solvent is relatively inferior in handleability compared to the case where aliphatic carboxylic acid ester is used. Also, when using an alcohol compound such as methanol and ethanol; or a ketone compound such as acetone and methyl ethyl ketone (MEK), which is commonly used in solvent polymerization in an effort to precipitate polymer, it significantly lowers the activity of the polymerization catalyst.

When precipitation polymerization is carried out in the method for producing the (co)polymer of the embodiment of the present invention, it is important to select a solvent which will not dissolve the generated polymer, will not make the surface of the precipitated polymer sticky and will not poison the catalyst from a viewpoint of reaction efficiency of polymerization, recovery of polymer, etc. As such a solvent, aliphatic carboxylic acid ester or a solvent containing aliphatic carboxylic acid ester is suitable.

While the solubility of the polymer is affected by the molecular structure of the polymer, the type of the polymerization catalyst and the like have a relatively small effect on the solubility, when there is not much difference in the composition and composition ratio of the monomer. Accordingly, when a (co)polymer containing monomer units represented by formula (2) and formula (3) is produced by precipitation polymerization using a polymerization catalyst other than that of the embodiment of the present invention, the above-mentioned solvents may be used. All the catalysts containing a nickel (Ni) compound or a palladium (Pd) compound capable of polymerizing a cyclic olefin compound, except for those which will be poisoned by aliphatic carboxylic acid ester and not exert the activity, may be used.

Main catalyst (A), cocatalyst (B) and phosphine ligand (C) are mixed when polymerization is performed. The order in which these are mixed is not particularly limited as long as main catalyst (A) is mixed with phosphine ligand (C) before (A) is placed in contact with cocatalyst (B). The component of main catalyst (A) and phosphine ligand (C) are mixed in advance and cocatalyst (B) is further added thereto to obtain a reaction composition and the composition may be added to a solution containing monomer to be polymerized. Also, cocatalyst (B) may be added to a solvent containing monomer to be polymerized, main catalyst (A) and phosphine ligand (C); or a mixture of main catalyst (A) and phosphine ligand (C) may be added to a mixture solution of monomer to be polymerized and cocatalyst (B).

In the embodiment of the present invention, it is preferable to mix main catalyst (A) and phosphine ligand (C) in advance to be in contact with each other for more than one minute, preferably for about 30 minutes to one hour and then mixed with cocatalyst (B) to be added to a reaction system containing cocatalyst (B); or to add a mixture of main catalyst (A) and phosphine ligand (C) to a reaction system containing cocatalyst (B). Such an operation enables exhibition of enhanced polymerization activity.

There is no particular limitation on the polymerization temperature but the temperature is generally from −100° C. to 150° C., preferably from −50° C. to 120° C. If the temperature is lower than −100° C., it lowers the polymerization rate. If the temperature is higher than 150° C., it lowers the catalytic activity in some cases. The polymerization rate and molecular weight can be controlled by selecting the polymerization temperature within the above-mentioned range.

The polymerization time is not particularly limited and, for example, from one minute to 100 hours. Also, it is preferable to conduct reaction under inert gas atmosphere such as nitrogen gas.

After the completion of the polymerization reaction, norbornene polymer as a reaction product can be subjected to post treatment by known operation and treating method (e.g. reprecipitation) and can be isolated through fractionation by filtration and subsequent drying.

In the norbornene copolymer composed of the monomer unit represented by formula (2) and formula (3) produced by the production method of the embodiment of the present invention, the content of the monomer unit represented by formula (2) is preferably 10 to 70 mol %. If the content of the monomer unit represented by formula (2) is less than 10 mol %, hydrophobicity of the copolymer increases, which decreases the solubility of the copolymer in the organic solvent while making the water absorption rate lower. On the other hand, if the content exceeds 70 mol %, the copolymer becomes hydrophilic, which increases the solubility of the copolymer in the organic solvent while making the water absorption rate higher. Accordingly, it is possible to control the solubility in the organic solvent and water absorption rate of the copolymer by adjusting the content of the monomer unit represented by formula (2).

In the norbornene copolymer composed of the monomer unit represented by formula (2) and formula (3) produced by the production method of the embodiment of the present invention, it is preferred that the content of the monomer unit represented by formula (2) be from 10 to 80 mol % in consideration for achieving a good balance between adequate solubility which is required when the norbornene copolymer of the embodiment of the present invention is formed into a film, a sheet and the like and low water absorption of the copolymer, more preferably 15 to 70 mol %, most preferably 20 to 60 mol %. The content of the monomer unit represented by formula (2) can be calculated from the integration value of $^1$H-NMR spectrum measured by dissolving the copolymer in powder form or film form in an appropriate deuterated solvent.

The norbornene (co)polymer produced by the production method of the embodiment of the present invention basically comprises norbornenes only. However, even so, it does not exclude the existence of a minute amount, e.g. 1 mol % or less, of the third monomer unit which would not affect the properties of the norbornene (co)polymer of the embodiment of the present invention. Also, the norbornene (co)polymer produced by the production method of the embodiment of the present invention may be copolymerized with a third monomer without undermining the effect of the present invention in an effort to improve the properties.

There is no particular limitation on the third monomer, and preferred are monomers having an ethylenic carbon-carbon double bond. Examples are α-olefins such as ethylene, propylene, 1-butene, 1-penetene and 1-hexene; aromatic vinyl compounds such as styrene, α-methylstyrene and divinylbenzene; chain conjugated dienes such as 1,3-butadiene and isoprene; vinyl ethers such as ethylvinyl ether and propylvinyl ether; acrylates such as methyl acrylate, ethyl acrylate and 2-ethylhexyl acrylate; and methacrylate such as methyl methacrylate and ethyl methacrylate. Among these, α-olefins such as ethylene, propylene and 1-hexene; and aromatic vinyl compounds such as styrene are particularly preferable.

In the norbornene copolymer produced by the production method of the embodiment of the present invention, the bonding mode of each of the monomer units may be random, block or alternate, depending on polymerization conditions. In consideration for enhancement in mechanical properties of the copolymer, random mode is preferred.

The number average molecular weight (Mn) of the norbornene (co)polymer produced by the production method of the embodiment of the present invention in terms of polystyrene measured by gel permeation chromatography (GPC) is preferably from 50,000 to 2,000,000, more preferably 100,000 to 1,500,000. If the number average molecular weight (Mn) in terms of polystyrene is less than 50,000, mechanical strength of the (co)polymer becomes insufficient. The number average molecular weight (Mn) in terms of polystyrene exceeding 2,000,000 not only lowers solvent solubility of the (co)polymer at the time of forming a cast film but also increases solution viscosity, which degrades molding workability of the (co)polymer. Also, the molecular weight distribution (Mw/Mn; weight average molecular weight/number average molecular weight) is preferably from 1.00 to 4.00, more preferably 1.30 to 3.50, still more preferably 1.50 to 3.30. If the (co)polymer has a wide molecular weight distribution range, the (co)polymer solution becomes less likely to be uniform at the time of forming a cast film, which makes it difficult to produce an excellent film.

Among the norbornene (co)polymers produced by the production method of the embodiment of the present invention, preferred is the polymer comprising the monomer units represented by formula (2) only

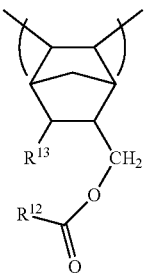

(2)

(symbols in the formula have the same meaning as mentioned above). The number average molecular weight (Mn) of the polymer is 200,000 to 1,000,000. When the number average molecular weight is less than 200,000, it lowers the chemical resistance while when the number average molecular weight exceeds 1,000,000, it not only decreases the solubility of the polymer in a solvent when forming a cast film but also increases the solution viscosity, to thereby lower the molding processability of the polymer.

The saturated water absorption of the norbornene (co)polymer produced by the production method of the embodiment of the present invention at 23° C. is generally from 0.001 to 1 mass %, preferably from 0.005 to 0.7 mass %, still more preferably from 0.01 to 0.5 mass %. When the saturated water absorption of the (co)polymer is within the above-mentioned range, various optical properties such as transparency, phase difference, uniformity of phase difference and dimensional accuracy of the (co)polymer are maintained even under conditions of high temperature and humidity. Therefore the products are excellent in adhesion properties to the other materials and will not experience peel-off while in use. Also, since the (co)polymer has good compatibility with additives such as an antioxidant, the (co)polymer allows increasing addition degree of freedom. The above-mentioned saturated water absorption is determined by dipping the (co)polymer in water at 23° C. for 24 hours and measuring the increased mass according to the method described in JIS K7209.

The glass-transition temperature (Tg) of the norbornene (co)polymer produced by the production method of the embodiment of the present invention may vary depending on the type of the monomer units which constitute the polymer, composition ratio (in the case where the polymer is a copolymer), and the presence or absence of the additives and the like, but is generally from 80 to 350° C., preferably from 100 to 320° C., still more preferably from 120 to 300° C. If Tg falls below the above-mentioned range, the heat distortion temperature becomes lower, which may cause a problem for heat resistance and optical properties of the obtained optical film may vary widely with temperature. If Tg is above the above-mentioned range, it increases the likelihood of heat deterioration of the (co)polymer when the (co)polymer is heated near to Tg during the stretching process.

The norbornene (co)polymer produced by the production method of the embodiment of the present invention can be processed into a film by the film formation according to a solution casting method. As a solvent to be used, toluene, tetrahydrofuran (THF), dichloromethane, chloroform and the like can be used.

EXAMPLES

Hereinafter, the present invention is described in more details by referring to Examples and Comparative Examples. The present invention is by no means limited thereto.

In each of Examples and Comparative Examples, the catalytic activity was determined by the following formula. However, in Comparative Example 6, "amount by mole of palladium" in the formula is replaced by "amount of nickel".

Catalytic activity=(the amount of the obtained polymer (g))/(amount by mole of palladium [mmol])  [Formula 1]

The weight average molecular weight (Mw), number average molecular weight (Mn) and molecular weight distribution (Mw/Mn) of the obtained polymer were determined by gel permeation chromatography (GPC) using polystyrene as a standard substance. The composition ratio of norbornene and 5-acetoxymethyl-2-norbornene (abbreviated as "ANB") in the copolymer was determined by the integration ratio of [$\delta$:3.5-4.5 ppm; "—$COOCH_2$—" unit of 5-acetoxymethyl-2-norbornene] and [$\delta$:0.5-3.0 ppm; "$CH_3COO$—", "—$CH_2$—" and "—CH=" units of norbornene (abbreviated as "NB") and 5-aceoxymethyl-2-norbornene] at the peak in $^1$H-NMR spectra. The ANB content rate was calculated by the following formula.

ANB content rate={(amount by mole of ANB units in the polymer)/(amount by mole of NB units in the polymer+amount by mole of ANB units in the polymer)}×100  [Formula 2]

Properties of the substances synthesized in Examples and Comparative Examples were measured as follows.
1. $^1$H-NMR, $^{13}$C-NMR
   Apparatus used: JEOL EX-400
   (400 MHz, manufactured by JEOL, LTD.)
Measurement method: measured by dissolving samples in deuterated chloroform and using tetramethylsilane as internal standard substance.
2. FT-IR
Apparatus used:
   System: Spectrum GX (manufactured by PerkinElmer, Inc.)
   ATR: MIRacle™ (manufactured by Pike Technologies)
Measurement Method:
   measured by a single reflection ATR method
3. Gel Permeation Chromatography (GPC)
Apparatus used:
   Column: Shodex GPC K-G+KF-806Lx2 (manufactured by SHOWA DENKO K.K.),
   Detector: Shodex SE-61 (manufactured by SHOWA DENKO K.K.),
Measurement Conditions
   Solvent: tetrahydrofuran,
   Measurement temperature: 40° C.,
   Flow rate: 1.0 ml/minute,
   Sample concentration: 1.0 mg/ml,
   Injection amount: 1.0 μl,
   Calibration curve: Universal Calibration curve,
   Analysis program: SIC 48011 (product of System Instruments, Inc.)
   Cyclopentadienyl(π-allyl)palladium was synthesized by the synthesis method as described in Shaw. B. L., Proc. Chem. Soc., 1960, 247.

Synthesis Example 1

Synthesis of 2-acetoxymethyl-5-norbornene

Dicyclopentadiene (manufactured by Tokyo Chemical Industry Co., Ltd.; 759.80 g, 5.747 mol), allyl acetate (manufactured by Tokyo Chemical Industry Co., Ltd., 1,457.86 g, 14.561 mol) and hydroquinone (manufactured by Wako Pure Chemical Industries Co., Ltd., 2.25 g, 0.0204 mol) were placed in a 10 liter-volume stainless-steel made autoclave. After the inside of the reaction system was substituted with nitrogen gas, the autoclave was heated to 190° C. while stirring the content at 500 rpm, and reaction was carried out for five hours. After the completion of the reaction, the autoclave was cooled to room temperature and the content was transferred to the distillation equipment to be distilled under reduced pressure. As a fraction at 0.07 kPa and 48° C., 1,306.70 g of a clear colorless liquid substance was obtained.

The $^1$H-NMR spectrum of the obtained liquid substance was measured and it was confirmed that the substance was the target 2-acetoxymethyl-5-norbornene. The molar ratio of exo isomer and endo isomer (exo/endo) of the obtained 2-acetoxymethyl-5-norbornene was 18/82.

Synthesis Example 2

Synthesis of 2-[N-(2,6-diisopropylphenyl)iminomethyl]phenol

Salicylaldehyde (manufactured by Tokyo Chemical Industry Co., Ltd.; 2.00 g, 16.4 mmol), 2,6-diisopropylaniline (manufactured by Tokyo Chemical Industry Co., Ltd.; 3.12 g, 17.6 mmol), ethanol (manufactured by Wako Pure Chemical Industries Co., Ltd.; 20 ml) and formic acid (manufactured by Wako Pure Chemical Industries Co., Ltd.; 305 mg, 6.63 mmol) were placed in one-neck flask, and the reaction was carried out at room temperature for one day while stirring the mixture. The precipitate was isolated by filtration and dissolved in methanol followed by recrystallization to obtain 1.79 g of yellow crystals. The $^{13}$C-NMR and $^{13}$C-NMR spectra of the obtained crystal were measured and it was confirmed that the crystal was 2-[N-(2,6-diisopropylphenyl)iminomethyl]phenol.

Synthesis Example 3

Synthesis of 2-[N-(2,6-diisopropylphenyl)iminomethyl]-4-fluorophenol 5-fluorosalicylaldehyde (manufactured by Tokyo Chemical Industry Co., Ltd.; 2.01 g, 14.3 mmol), 2,6-diisopropylaniline (manufactured by Tokyo Chemical Industry Co., Ltd.; 2.82 g, 15.9 mmol), ethanol (manufactured by Wako Pure Chemical Industries Co., Ltd.; 20 ml) and formic acid (manufactured by Wako Pure Chemical Industries Co., Ltd.; 305 mg, 6.63 mmol) were placed in one-neck flask, and the reaction was carried out at room temperature for one day while stirring the mixture. The precipitate was isolated by filtration and dissolved in methanol followed by recrystallization to obtain 2.10 g of yellow crystals. The $^{13}$C-NMR and $^{13}$C-NMR spectra of the obtained crystal were measured and it was confirmed that the crystal was 2-[N-(2,6-diisopropylphenyl)iminomethyl]-4-fluorophenol.

Synthesis Example 4

Synthesis of 2-(N-phenyliminomethyl)phenol

Salicylaldehyde (manufactured by Tokyo Chemical Industry Co., Ltd.; 2.00 g, 16.4 mmol), ethanol (manufactured by Wako Pure Chemical Industries Co., Ltd.; 20 ml), aniline (manufactured by Wako Pure Chemical Industries Co., Ltd.; 1.70 g, 18.4 mmol) and formic acid (manufactured by Wako Pure Chemical Industries Co., Ltd.; 305 mg, 6.63 mmol) were placed in one-neck flask, and the reaction was carried out at room temperature for one day while stirring the mixture. The precipitate was isolated by filtration and dissolved in n-hexane followed by recrystallization to obtain 1.36 g of yellow crystals. The $^1$H-NMR and $^{13}$C-NMR spectra of the obtained crystal were measured and it was confirmed that the crystal was 2-(N-phenyliminomethyl)phenol.

Synthesis Example 5

Synthesis of 2-[N-(2,6-diisopropylphenyl)iminomethyl]-6-methylphenol 6-methylsalicylaldehyde (manufactured by Sigma-Aldrich; 881 mg, 6.47 mmol), 2,6-diisopropylaniline (manufactured by Tokyo Chemical Industry Co., Ltd.; 1.15 g, 6.49 mmol), ethanol (manufactured by Wako Pure Chemical Industries Co., Ltd.; 10 ml) and formic acid (manufactured by Wako Pure Chemical Industries Co., Ltd.; 159 mg, 3.45 mmol) were placed in one-neck flask, and the reaction was carried out at room temperature for one day while stirring the mixture. The precipitate was isolated by filtration and dissolved in ethanol followed by recrystallization to obtain 1.31 g of yellow crystals. The $^1$H-NMR and $^{13}$C-NMR spectra of the obtained crystal were measured and it was confirmed that the crystal was 2-[N-(2,6-diisopropylphenyl)iminomethyl]-6-methylphenol.

Example 1

Synthesis of (π-allyl){2-[N-(2,6-diisopropylphenyl)iminomethyl]phenolate}palladium (Complex A-1)

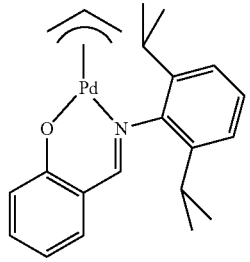

[Complex A-1]

After the inside of a two-neck flask equipped with a three-way stopcock was substituted with nitrogen, 2-[N-(2,6-diisopropylphenyl)iminomethyl]phenol prepared in Synthesis Example 2 (506 mg, 1.80 mmol) was added thereto and dissolved in anhydrous tetrahydrofuran (manufactured by Wako Pure Chemical Industries Co., Ltd.; 20 ml). After the resultant mixture was dipped in a dry ice-ethanol bath and cooled to −78° C., a solution of 1.6 mol n-butyllithium in 1 l of hexane (manufactured Wako Pure Chemical Industries Co., Ltd.; 1.14 ml, 1.82 mmol) was delivered slowly by drops into the mixture for five minutes. After the instillation was completed, the mixture was gradually restored to room temperature.

After the inside of a two-neck flask equipped with a three-way stopcock as separately prepared was substituted with nitrogen, allylpalladium chloride dimer (manufactured by Wako Pure Chemical Industries Co., Ltd.; 305 mg, 0.834 mmol) was charged into the flask and dissolved in anhydrous dichloromethane (manufactured by Wako Pure Chemical Industries Co., Ltd.; 20 ml).

Figure 2:
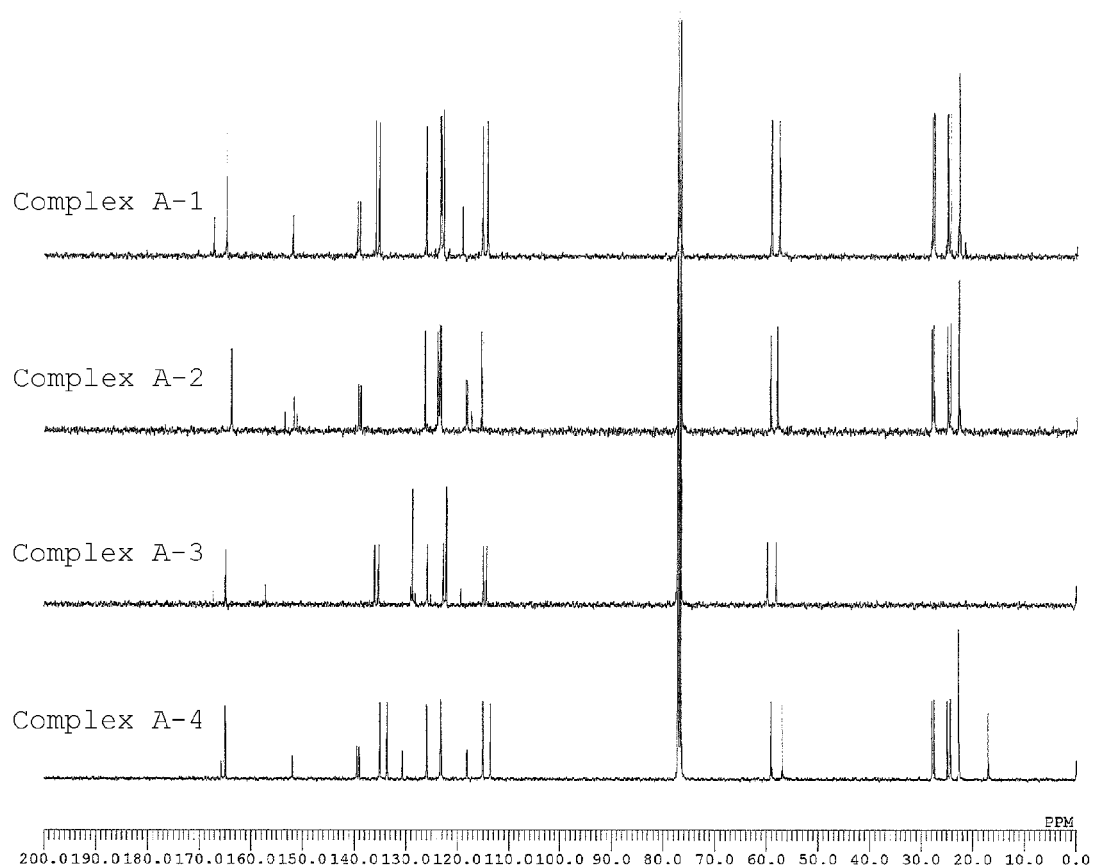
FIG. 2 is a $^{13}$C-NMR spectrum of the complex obtained in Examples 1 to 4.

The solution was dipped in an ice bath to be cooled to 0° C. and a mixed solution of tetrahydrofuran/hexane prepared in advance was delivered slowly by drops for five minutes to carry out the reaction at 0° C. for two hours. After that, the solvent was completely distilled away under reduced pressure. After newly adding anhydrous toluene (manufactured by Wako Pure Chemical Industries Co., Ltd.; 20 ml) thereto followed by stirring, the solution was subjected to centrifugation under nitrogen atmosphere to thereby remove unnecessary salts and recover the supernatant toluene solution. The solution was condensed under reduced pressure followed by recrystallization to obtain 356 mg of yellow crystals. The $^1$H-NMR, $^{13}$C-NMR and IR spectra of the obtained crystal were measured and it was confirmed that the crystal was (π-allyl){2-[N-(2,6-diisopropylphenyl)iminomethyl]

phenolate}palladium (Complex A-1). The $^1$H-NMR spectrum and $^{13}$C-NMR spectrum are shown in FIG. 1 and FIG. 2, respectively.

Example 2

Synthesis of (π-allyl){2-[N-(2,6-diisopropylphenyl)iminomethyl]-4-fluorophenolate}palladium (Complex A-2)

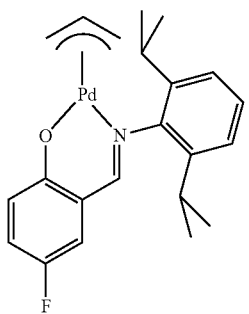

[Complex A-2]

After the inside of a two-neck flask equipped with a three-way stopcock was substituted with nitrogen, 2-[N-(2,6-diisopropylphenyl)iminomethyl]-4-fluorophenol prepared in Synthesis Example 3 (503 mg, 1.68 mmol) was added thereto and dissolved in anhydrous tetrahydrofuran (manufactured by Wako Pure Chemical Industries Co., Ltd.; 10 ml). After the resultant mixture was dipped in a dry ice-ethanol bath and cooled to −78° C., a solution of 1.6 mol n-butyllithium in 1 l of hexane (manufactured Wako Pure Chemical Industries Co., Ltd.; 1.10 ml, 1.76 mmol) was delivered slowly by drops into the mixture for five minutes. After the instillation was completed, the mixture was stirred at −78° C. for 15 minutes and then gradually restored to room temperature.

After the inside of a two-neck flask equipped with a three-way stopcock as separately prepared was substituted with nitrogen, allylpalladium chloride dimer (manufactured by Wako Pure Chemical Industries Co., Ltd.; 301 mg, 0.823 mmol) was charged into the flask and dissolved in anhydrous dichloromethane (manufactured by Wako Pure Chemical Industries Co., Ltd.; 10 ml).

The solution was dipped in a dry ice-ethanol bath to be cooled to −78° C. and into the solution a mixed solution of tetrahydrofuran/hexane prepared in advance was delivered slowly by drops for five minutes. Then the solution temperature was gradually restored to 0° C. for 90 minutes. After that, the solvent was completely distilled away under reduced pressure. After newly adding anhydrous toluene (manufactured by Wako Pure Chemical Industries Co., Ltd.; 20 ml) thereto followed by stirring, the solution was subjected to centrifugation under nitrogen atmosphere to thereby remove unnecessary salts and recover the supernatant toluene solution. The solution was condensed under reduced pressure followed by recrystallization to obtain 297 mg of yellow crystals. The $^1$H-NMR and $^{13}$C-NMR spectra of the obtained crystal were measured and it was confirmed that the crystal was (π-allyl){2-[N-(2,6-diisopropylphenyl)iminomethyl]-4-fluorophenolate}palladium (Complex A-2). The $^1$H-NMR spectrum and $^{13}$C-NMR spectrum are shown in FIG. 1 and FIG. 2, respectively.

Example 3

Synthesis of (π-allyl)[2-(N-phenyliminomethyl)phenolate]palladium (Complex A-3)

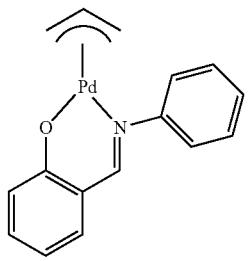

[Complex A-3]

After the inside of a two-neck flask equipped with a three-way stopcock was substituted with nitrogen, 2-(N-phenyliminomethyl)phenol prepared in Synthesis Example 4 (329 mg, 1.67 mmol) was added thereto and dissolved in anhydrous tetrahydrofuran (manufactured by Wako Pure Chemical Industries Co., Ltd.; 10 ml). After the resultant mixture was dipped in a dry ice-ethanol bath and cooled to −78° C., a solution of 1.6 mol n-butyllithium in 1 l of hexane (manufactured Wako Pure Chemical Industries Co., Ltd.; 1.10 ml, 1.76 mmol) was delivered slowly by drops into the mixture for five minutes. After the instillation was completed, the mixture was stirred at −78° C. for 30 minutes and then gradually restored to room temperature.

After the inside of a two-neck flask equipped with a three-way stopcock as separately prepared was substituted with nitrogen, allylpalladium chloride dimer (manufactured by Wako Pure Chemical Industries Co., Ltd.; 303 mg, 0.827 mmol) was charged into the flask and dissolved in anhydrous dichloromethane (manufactured by Wako Pure Chemical Industries Co., Ltd.; 10 ml).

The solution was dipped in a dry ice-ethanol bath to be cooled to −78° C. and into the solution a mixed solution of tetrahydrofuran/hexane prepared in advance was delivered slowly by drops for five minutes. Then the solution temperature was restored to 0° C. and the solution was stirred for 30 minutes. After that, the solvent was completely distilled away under reduced pressure. After newly adding anhydrous toluene (manufactured by Wako Pure Chemical Industries Co., Ltd.; 20 ml) thereto followed by stirring, the solution was subjected to centrifugation under nitrogen atmosphere to thereby remove unnecessary salts and recover the supernatant toluene solution. The solution was condensed under reduced pressure followed by recrystallization to obtain 87 mg of yellow crystals. The $^1$H-NMR and $^{13}$C-NMR spectra of the obtained crystal were measured and it was confirmed that the crystal was (π-allyl)[2-(N-phenyliminomethyl)phenolate]

palladium (Complex A-3). The $^1$H-NMR spectrum and $^{13}$C-NMR spectrum are shown in FIG. 1 and FIG. 2, respectively.

Example 4

Synthesis of (π-allyl){2-[N-(2,6-diisopropylphenyl)iminomethyl]-6-methylphenolate}palladium (Complex A-4)

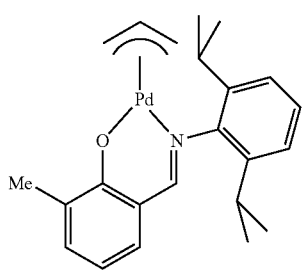

[Complex A-4]

After the inside of a two-neck flask equipped with a three-way stopcock was substituted with nitrogen, 2-[N-(2,6-diisopropylphenyl)iminomethyl]-6-methylphenol prepared in Synthesis Example 5 (495 mg, 1.67 mmol) was added thereto and dissolved in anhydrous tetrahydrofuran (manufactured by Wako Pure Chemical Industries Co., Ltd.; 10 ml). After the resultant mixture was dipped in a dry ice-ethanol bath and cooled to −78° C., a solution of 1.6 mol n-butyllithium in 1 l of hexane (manufactured Wako Pure Chemical Industries Co., Ltd.; 1.10 ml, 1.76 mmol) was delivered slowly by drops into the mixture for five minutes. After the instillation was completed, the mixture was stirred at −78° C. for 20 minutes and then gradually restored to −10° C.

After the inside of a two-neck flask equipped with a three-way stopcock as separately prepared was substituted with nitrogen, allylpalladium chloride dimer (manufactured by Wako Pure Chemical Industries Co., Ltd.; 303 mg, 0.827 mmol) was charged into the flask and dissolved in anhydrous dichloromethane (manufactured by Wako Pure Chemical Industries Co., Ltd.; 10 ml).

The solution was dipped in a dry ice-ethanol bath to be cooled to −78° C. and into the solution a mixed solution of tetrahydrofuran/hexane prepared in advance was delivered slowly by drops for five minutes. Then the solution was stirred at −78° C. for two hours to be reacted. After that, the solvent was completely distilled away under reduced pressure. After newly adding anhydrous toluene (manufactured by Wako Pure Chemical Industries Co., Ltd.; 20 ml) thereto followed by stirring, the solution was subjected to centrifugation under nitrogen atmosphere to thereby remove unnecessary salts and recover the supernatant toluene solution. The solution was condensed under reduced pressure followed by recrystallization to obtain 197 mg of yellow crystals. The $^1$H-NMR and $^{13}$C-NMR spectra of the obtained crystal were measured and it was confirmed that the crystal was (π-allyl){2-[N-(2,6-diisopropylphenyl)iminomethyl]-6-methylphenolate}palladium (Complex A-4). The $^1$H-NMR spectrum and $^{13}$C-NMR spectrum are shown in FIG. 1 and FIG. 2, respectively.

Example 5

Addition copolymerization of norbornene and 2-acetoxymethyl-5-norbornene

After the inside of a three-neck flask equipped with a three-way stopcock and a mechanical stirrer was substituted with nitrogen, norbornene (manufactured by Tokyo Chemical Industry Co., Ltd.; 4.71 g, 0.050 mol) and 2-acetoxymethyl-5-norbornene prepared in Synthesis Example 1 (16.62 g, 0.100 mol) were added thereto and dissolved in 75 ml of toluene. After further adding thereto a solution of N,N-dimethylaniliumtetrakis(pentafluorophenyl)borate [($C_6H_5$)($CH_3$)$_2$NH][B($C_6F_5$)$_4$] (manufactured by Strem Chemicals, Inc.; 8.0 mg, 0.010 mmol) dissolved in 1 ml of dichloromethane, the resultant solution was heated to 70° C. To the solution, a catalyst solution of (π-allyl){2-[N-(2,6-diisopropylphenyl)iminomethyl]phenolate}palladium (Complex A-1) (4.3 mg, 0.010 mmol) synthesized in Example 1 and prepared in another vessel and triisopropyl phosphine [P(i-$C_3H_7$)$_3$] (manufactured by Strem Chemicals, Inc.; 1.6 mg, 0.010 mmol) dissolved in 3.5 ml of toluene was added, thereby carrying out polymerization reaction at 70° C. for 30 minutes. After that, a solution of norbornene as prepared separately (Tokyo Chemical Industries Co., Ltd.; 4.71 g, 0.050 ml) dissolved in 5.4 ml of toluene was added to the reaction solution, thereby carrying out polymerization reaction at 70° C. for another 30 minutes. After the reaction was completed, 8 ml of methanol added with small quantity of hydrochloric acid was added to the reaction solution to thereby terminate the reaction. Next, the reaction solution was diluted with toluene and put into large quantity of methanol to precipitate polymers. The precipitated polymer was separated by filtration followed by washing, and then dried at 90° C. under reduced pressure for five hours to obtain 10.52 g of polymer in the white powder form. The catalytic activity calculated based on the polymer yield and the charge of the catalyst was 1052 g of polymer/mmol of palladium (Pd).

Figure 3:
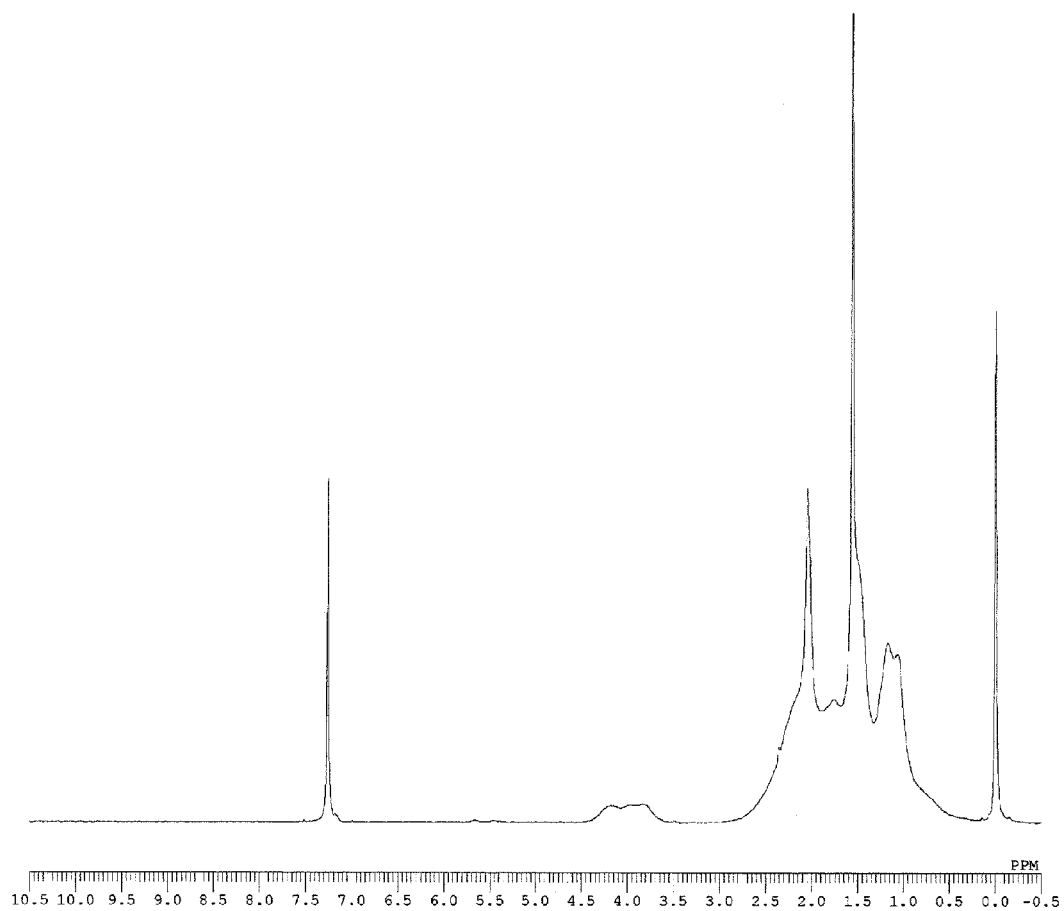
FIG. 3 is a $^1$H-NMR Spectrum of the copolymer obtained in Example 5.
Figure 4:
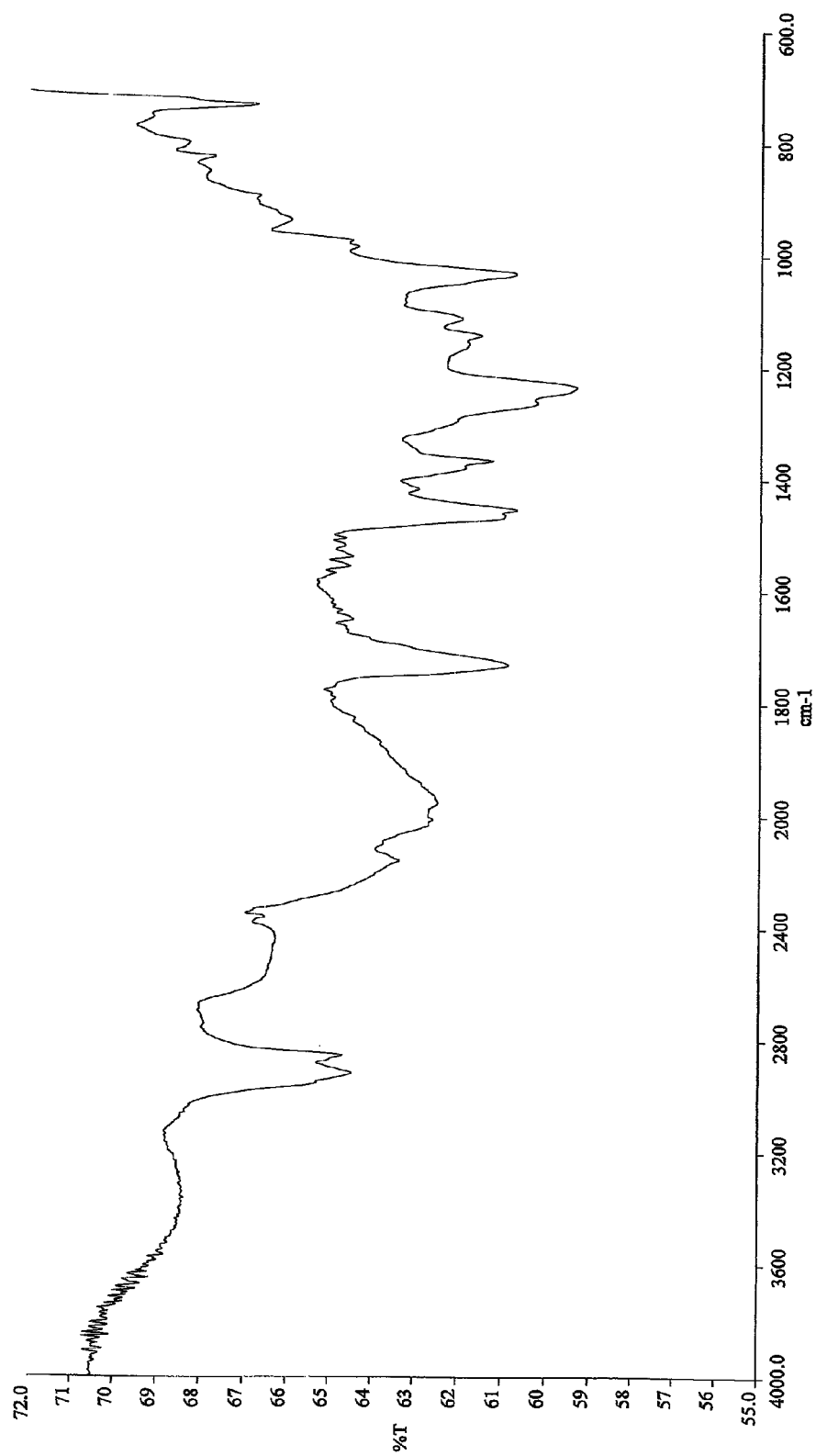
FIG. 4 is an IR Spectrum of the copolymer obtained in Example 5.
Figure 5:
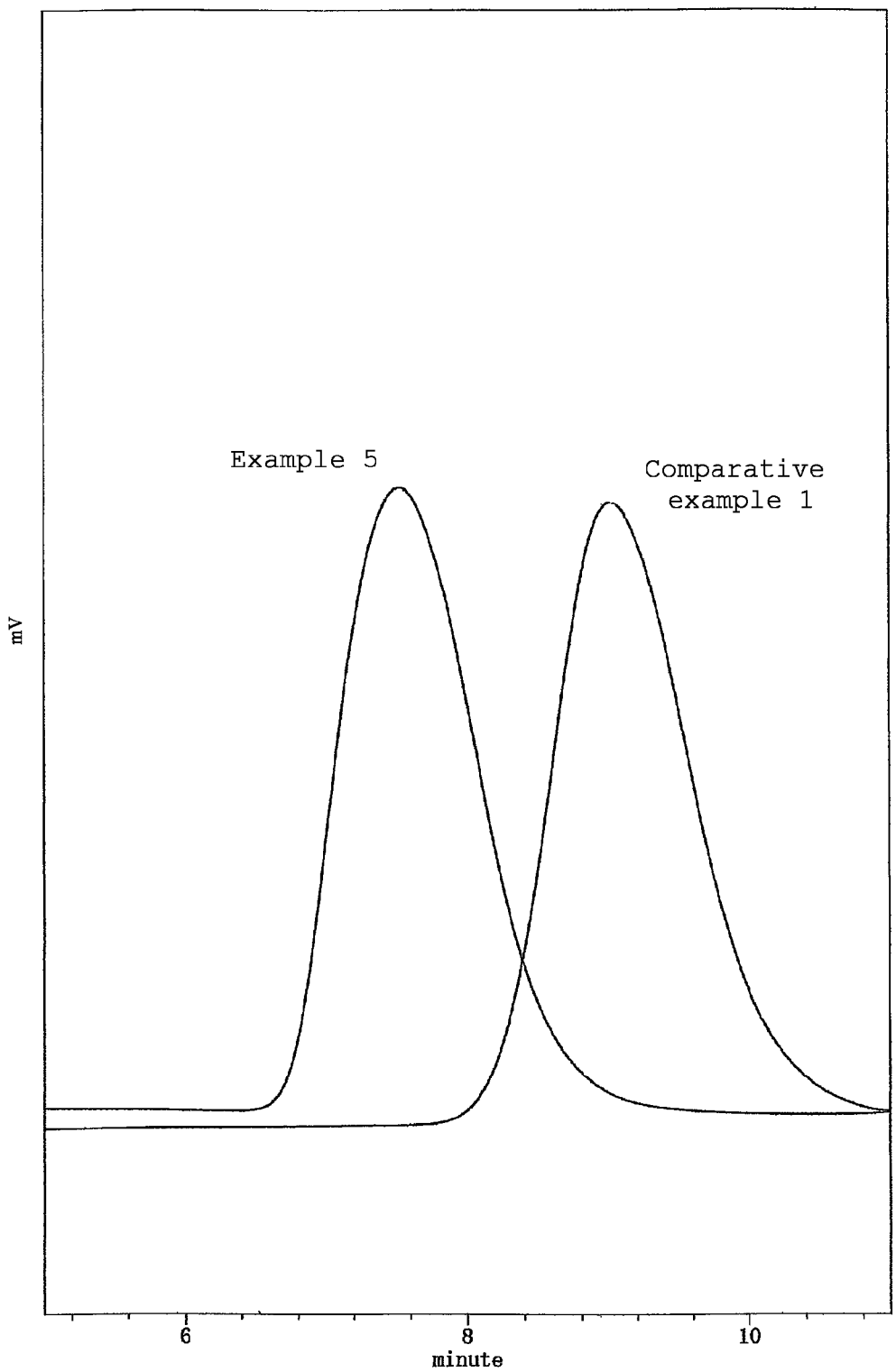
FIG. 5 is a gel permeation chromatography (GPC) chart of the copolymers obtained in Example 5 and Comparative Example 1.

The obtained polymer was easily dissolved in a general solvent such as THF and chloroform and had a number average molecular weight (Mn) of 916,000 and a molecular distribution (Mw/Mn) of 2.12. The composition ratio of the 2-acetoxymethyl-5-norbornene monomer unit in the polymer calculated by the integral value of the $^1$H-NMR spectrum was 20.4 mol %. $^1$H-NMR spectrum, IR spectrum and the gel permeation chromatography (GPC) chart are shown in FIG. 3, FIG. 4 and FIG. 5, respectively.

Examples 6 to 7

Polymerization was carried out in the same way as in Example 5 except that the polymerization temperature was controlled to 80° C. and 90° C. as in Table 1.

Examples 8 to 10

Polymerization was carried out in the same way as in Example 6 except that cocatalyst (B) and phosphine ligand (C) were changed to those shown in Table 1.

Example 11

Addition copolymerization of norbornene and 2-acetoxymethyl-5-norbornene

After the inside of a three-neck flask equipped with a three-way stopcock and a mechanical stirrer was substituted with nitrogen, norbornene (manufactured by Tokyo Chemical Industry Co., Ltd.; 4.71 g, 0.050 mol) and 2-acetoxymethyl-5-norbornene prepared in Synthesis Example 1 (16.62 g, 0.100 mol) were added thereto and dissolved in 75 ml of toluene. After further adding thereto a solution of N,N-dimethylaniliumtetrakis(pentafluorophenyl)borate [($C_6H_5$)($CH_3$)$_2$NH][B($C_6F_5$)$_4$] (manufactured by Strem Chemicals, Inc.; 8.0 mg, 0.010 mmol) dissolved in 1 ml of dichloromethane, the resultant solution was heated to 80° C. A catalyst solution of (π-allyl){2-[N-(2,6-diisopropylphenyl)iminomethyl]phenolate}palladium (Complex A-1) (4.3 mg, 0.010 mmol) synthesized in Example 1 and prepared in another vessel and triisopropyl phosphine [P(i-C$_3$H$_7$)$_3$] (manufactured by Strem Chemicals, Inc.; 1.6 mg, 0.010 mmol) dissolved in 3.5 ml of toluene was added to the reaction solution, thereby initiating polymerization. Subsequently, while adding a solution of norbornene as prepared separately (Tokyo Chemical Industries Co., Ltd.; 4.71 g, 0.050 ml) dissolved in 5.4 ml of toluene five times every 30 minutes and 5-acetoxymethyl-2-norbornene (5.00 g, 0.030 mol) two times at hourly intervals to the reaction solution, the polymerization reaction was carried out at 80° C. for three hours in total. After the reaction was completed, 8 ml of methanol added with small quantity of hydrochloric acid was added to the reaction solution to thereby terminate the reaction. Next, the reaction solution was diluted with toluene and put into large quantity of methanol to precipitate polymers. The precipitated polymer was separated by filtration followed by washing, and then dried at 90° C. under reduced pressure for five hours to obtain 33.90 g of polymer in the white powder form. The catalytic activity calculated based on the polymer yield and the charge of the catalyst was 3390 g of polymer/mmol of palladium (Pd).

The obtained polymer was easily dissolved in a general solvent such as THF and chloroform and had a number average molecular weight (Mn) of 283,400 and a molecular distribution (Mw/Mn) of 3.12. The composition ratio of the 2-acetoxymethyl-5-norbornene monomer unit in the polymer calculated by the integral value of the $^1$H-NMR spectrum was 19.3 mol %.

Examples 12 to 14

Polymerization was carried out in the same way as in Example 11 except that the polymerization temperature and the charges of metal complex (A), cocatalyst (B) and phosphine ligand (C) were changed to those shown in Table 1.

Example 15

Addition copolymerization of norbornene and 2-acetoxymethyl-5-norbornene

After the inside of a three-neck flask equipped with a three-way stopcock and a mechanical stirrer was substituted with nitrogen, norbornene (manufactured by Tokyo Chemical Industry Co., Ltd.; 4.71 g, 0.050 mol) and 2-acetoxymethyl-5-norbornene prepared in Synthesis Example 1 (16.62 g, 0.100 mol) were added thereto and dissolved in 75 ml of toluene. After adding a catalyst solution of (π-allyl){2-[N-(2,6-diisopropylphenyl)iminomethyl]phenolate}palladium (Complex A-1) (4.3 mg, 0.010 mmol) synthesized in Example 1 dissolved in 1.0 ml of toluene and triisopropyl phosphine [P(i-C$_3$H$_7$)$_3$] (manufactured by Strem Chemicals, Inc.; 1.6 mg, 0.010 mmol) dissolved in 1.0 ml of toluene, the resultant solution was heated to 80° C. After adding thereto a solution of N,N-dimethylaniliumtetrakis(pentafluorophenyl)borate [(C$_6$H$_5$)(CH$_3$)$_2$NH][B(C$_6$F$_5$)$_4$] (manufactured by Strem Chemicals, Inc.; 8.0 mg, 0.010 mmol) dissolved in 1 ml of dichloromethane, thereby initiating polymerization, and polymerization reaction was carried out at 80° C. for 30 minutes. Subsequently, a solution of norbornene as prepared separately (Tokyo Chemical Industries Co., Ltd.; 4.71 g, 0.050 ml) dissolved in 5.4 ml of toluene was added thereto and the polymerization reaction was carried out at 80° C. for another 30 minutes. After the reaction was completed, 8 ml of methanol added with small quantity of hydrochloric acid was added to the reaction solution to thereby terminate the reaction. Next, the reaction solution was diluted with toluene and put into large quantity of methanol to precipitate polymers. The precipitated polymer was separated by filtration followed by washing, and then dried at 90° C. under reduced pressure for five hours to obtain 4.30 g of polymer in the white powder form. The catalytic activity calculated based on the polymer yield and the charge of the catalyst was 430 g of polymer/mmol of palladium (Pd).

The obtained polymer was easily dissolved in a general solvent such as THF and chloroform and had a number average molecular weight (Mn) of 355,000 and a molecular distribution (Mw/Mn) of 2.84. The composition ratio of the 2-acetoxymethyl-5-norbornene monomer unit in the polymer calculated by the integral value of the $^1$H-NMR spectrum was 17.9 mol %.

Example 16

Addition copolymerization of norbornene and 2-acetoxymethyl-5-norbornene

After the inside of a three-neck flask equipped with a three-way stopcock and a mechanical stirrer was substituted with nitrogen, norbornene (manufactured by Tokyo Chemical Industry Co., Ltd.; 4.71 g, 0.050 mol) and 2-acetoxymethyl-5-norbornene prepared in Synthesis Example 1 (16.62 g, 0.100 mol) were added thereto and dissolved in 75 ml of toluene. After further adding thereto a solution of N,N-dimethylaniliumtetrakis(pentafluorophenyl)borate [(C$_6$H$_5$)(CH$_3$)$_2$NH][B(C$_6$F$_5$)$_4$] (manufactured by Strem Chemicals, Inc.; 8.0 mg, 0.010 mmol) dissolved in 1 ml of dichloromethane, the resultant solution was heated to 60° C. After adding a catalyst solution of (π-allyl){2-[N-(2,6-diisopropylphenyl)iminomethyl]-4-fluorophenolate}palladium (Complex A-2) (4.5 mg, 0.010 mmol) synthesized in Example 2 and prepared in another vessel and triisopropyl phosphine [P(i-C$_3$H$_7$)$_3$] (manufactured by Strem Chemicals, Inc.; 1.6 mg, 0.010 mmol) dissolved in 3.5 ml of toluene, polymerization reaction was carried out at 60° C. for 30 minutes. Subsequently, a solution of norbornene as prepared separately (Tokyo Chemical Industries Co., Ltd.; 4.71 g, 0.050 ml) dissolved in 5.4 ml of toluene was added thereto and the polymerization reaction was carried out at 60° C. for another 30 minutes. After the reaction was completed, 8 ml of methanol added with small quantity of hydrochloric acid was added to the reaction solution to thereby terminate the reaction. Next, the reaction solution was diluted with toluene and put into large quantity of methanol to precipitate polymers. The precipitated polymer was separated by filtration followed by washing, and then dried at 90° C. under reduced pressure for five hours to obtain 13.58 g of polymer in the white powder form. The catalytic activity calculated based on the polymer yield and the charge of the catalyst was 1358 g of polymer/mmol of palladium (Pd).

The obtained polymer was easily dissolved in a general solvent such as THF and chloroform and had a number average molecular weight (Mn) of 817,000 and a molecular distribution (Mw/Mn) of 2.07. The composition ratio of the 2-acetoxymethyl-5-norbornene monomer unit in the polymer calculated by the integral value of the $^1$H-NMR spectrum was 31.2 mol %.

Examples 17 to 23

Polymerization was carried out in the same way as in Example 16 except that the polymerization temperature and the charges of cocatalyst (B) and the monomer were changed to those shown in Table 1.

Example 24

Addition copolymerization of norbornene and 2-acetoxymethyl-5-norbornene

Polymerization reaction and posttreatment were performed in the same way as in Example 5 except that (π-allyl){2-[N-(2,6-diisopropylphenyl)iminomethyl]phenolate}palladium (Complex A-1) (4.3 mg, 0.010 mmol) was substituted with (π-allyl)[2-(N-phenyliminomethyl)phenolate]palladium (Complex A-3) (3.4 mg, 0.010 mmol) synthesized in Example 3 and the polymerization temperature was controlled to 80° C. to obtain 17.62 g of polymer in the white powder form. The catalytic activity calculated based on the polymer yield and the charge of the catalyst was 1762 g of polymer/mmol of palladium (Pd).

The obtained polymer was easily dissolved in a general solvent such as THF and chloroform and had a number average molecular weight (Mn) of 460,000 and a molecular distribution (Mw/Mn) of 2.28. The composition ratio of the 2-acetoxymethyl-5-norbornene monomer unit in the polymer calculated by the integral value of the $^1$H-NMR spectrum was 27.6 mol %.

Examples 25 to 29

Polymerization was carried out in the same way as in Example 24 except that the charge of the monomer, polymerization temperature and reaction time were changed to those shown in Table 1.

Example 30

Addition copolymerization of norbornene and 2-acetoxymethyl-5-norbornene

Polymerization reaction and posttreatment were performed in the same way as in Example 21 except that (π-allyl){2-[N-(2,6-diisopropylphenyl)iminomethyl]phenolate}palladium (Complex A-1) (4.3 mg, 0.010 mmol) was substituted with (π-allyl){2-[N-(2,6-diisopropylphenyl)iminomethyl]-6-methylphenolate}palladium (Complex A-4) (4.4 mg, 0.010 mmol) synthesized in Example 4 to obtain 19.02 g of polymer in the white powder form. The catalytic activity calculated based on the polymer yield and the charge of the catalyst was 1902 g of polymer/mmol of palladium (Pd).

The obtained polymer was easily dissolved in a general solvent such as THF and chloroform and had a number average molecular weight (Mn) of 720,000 and a molecular distribution (Mw/Mn) of 2.20. The composition ratio of the 2-acetoxymethyl-5-norbornene monomer unit in the polymer calculated by the integral value of the $^1$H-NMR spectrum was 25.4 mol %.

Examples 31 to 33

Polymerization was carried out in the same way as in Example 30 except that the polymerization temperature and reaction time were changed to those shown in Table 1.

Example 34

Addition homopolymerization of 2-acetoxymethyl-5-norbornene

After the inside of a three-neck flask equipped with a three-way stopcock and a mechanical stirrer was substituted with nitrogen, 2-acetoxymethyl-5-norbornene prepared in Synthesis Example 1 (16.62 g, 0.100 mol) was added thereto. After further adding thereto a solution of N,N-dimethylaniliumtetrakis(pentafluorophenyl)borate [(C$_6$H$_5$)(CH$_3$)$_2$NH][B(C$_6$F$_5$)$_4$] (manufactured by Strem Chemicals, Inc.; 8.0 mg, 0.010 mmol) dissolved in 1 ml of dichloromethane, the resultant solution was heated to 80° C. After adding a catalyst solution of (π-allyl){2-[N-(2,6-diisopropylphenyl)iminomethyl]phenolate}palladium (Complex A-1) (4.3 mg, 0.010 mmol) synthesized in Example 1 and prepared separately, and triisopropyl phosphine [P(i-C$_3$H$_7$)$_3$] (manufactured by Strem Chemicals, Inc.; 1.6 mg, 0.010 mmol) dissolved in 3.5 ml of toluene, the polymerization reaction was performed at 80° C. for 60 minutes. After the reaction was completed, 8 ml of methanol added with small quantity of hydrochloric acid was added to the reaction solution to thereby terminate the reaction. Next, the reaction solution was diluted with toluene and put into large quantity of methanol to precipitate polymers. The precipitated polymer was separated by filtration followed by washing, and then dried at 90° C. under reduced pressure for five hours to obtain 6.59 g of polymer in the white powder form. The catalytic activity calculated based on the polymer yield and the charge of the catalyst was 659 g of polymer/mmol of palladium (Pd).

Figure 6:
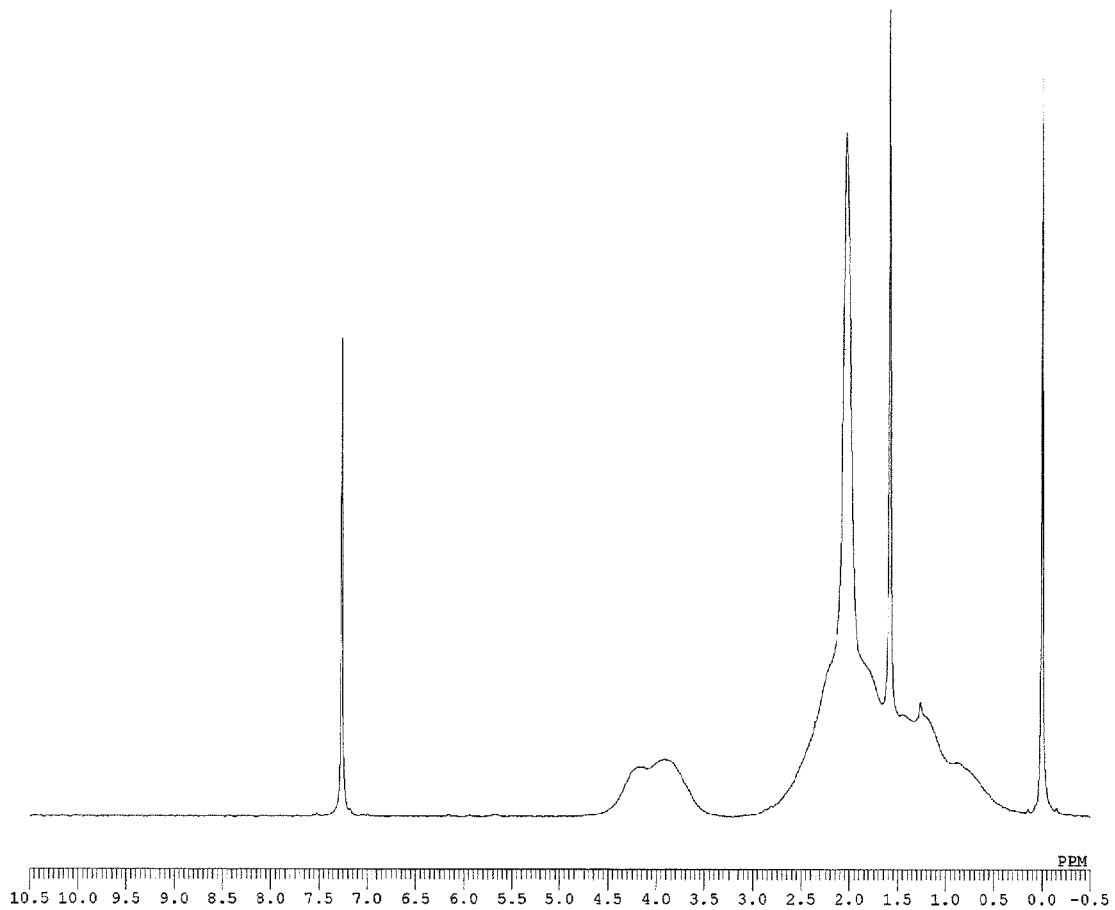
FIG. 6 is a $^1$H-NMR spectrum of the homopolymer obtained in Example 34.
Figure 7:
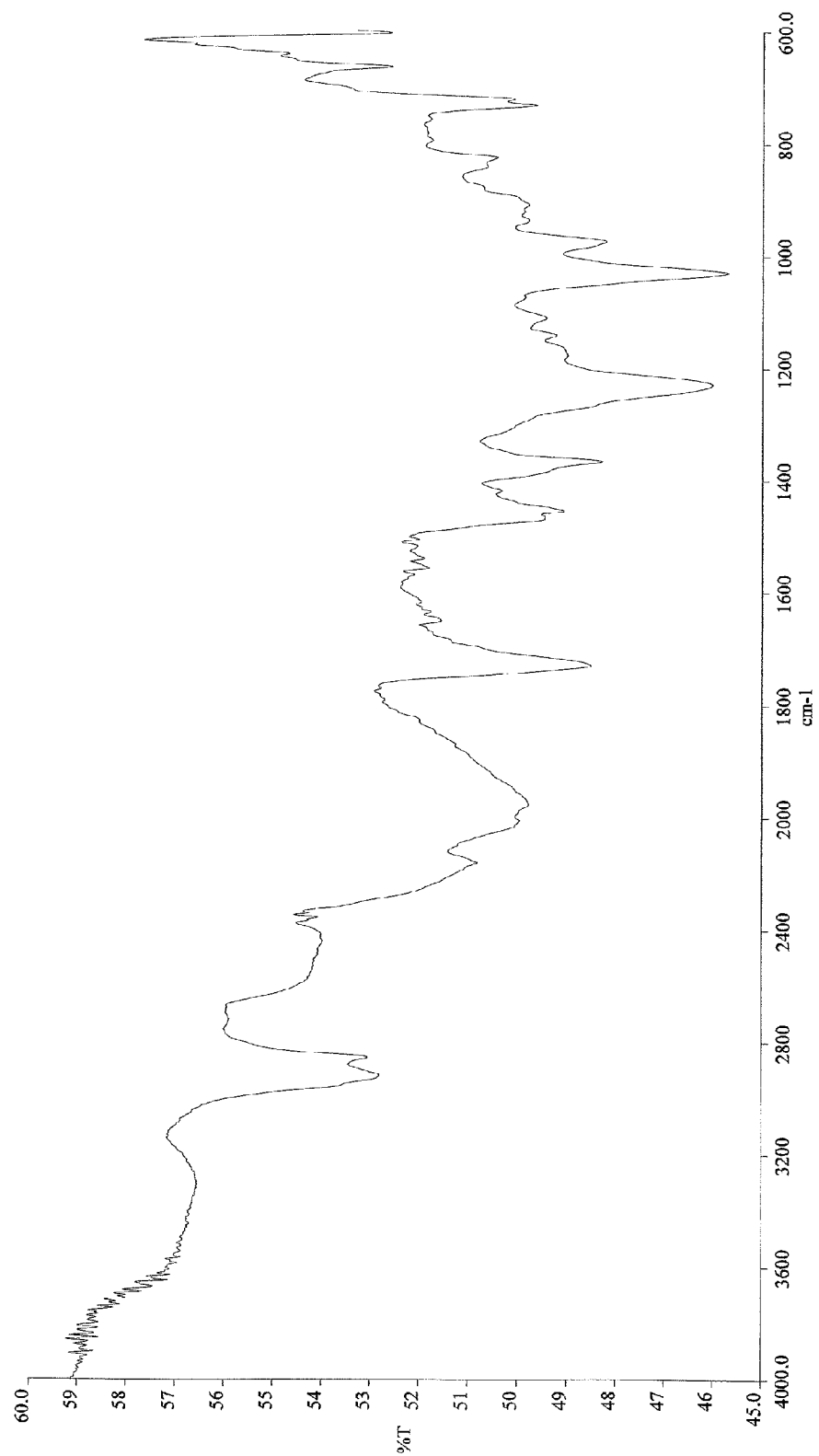
FIG. 7 is a IR spectrum of the homopolymer obtained in Example 34.
Figure 8:
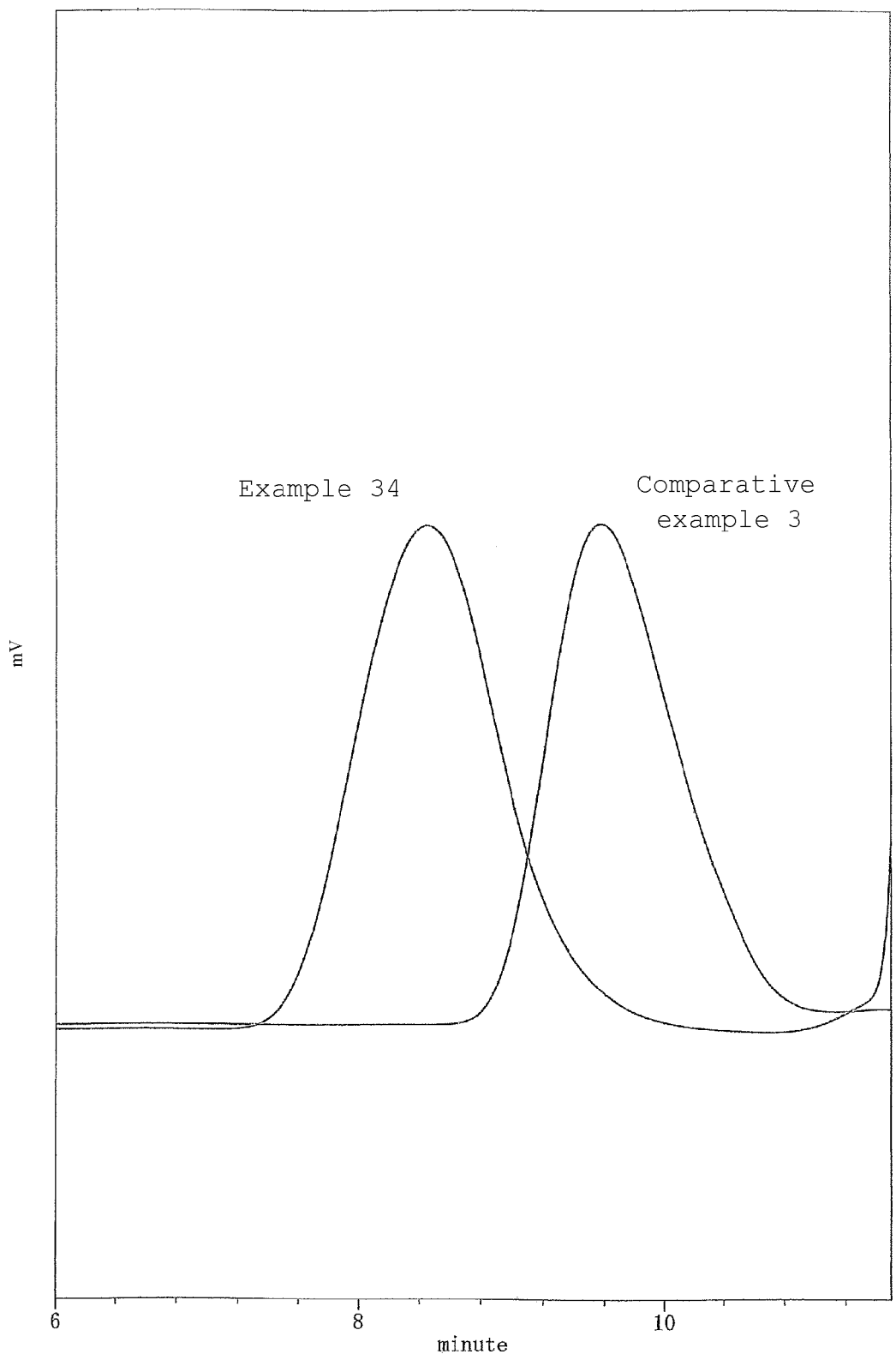
FIG. 8 is a gel permeation chromatography (GPC) chart of the homopolymers obtained in Example 34 and Comparative Example 3.

The obtained polymer was easily dissolved in a general solvent such as THF and chloroform and had a number average molecular weight (Mn) of 208,000 and a molecular distribution (Mw/Mn) of 2.05. $^1$H-NMR spectrum, IR spectrum and the gel permeation chromatography (GPC) chart are shown in FIG. 6, FIG. 7 and FIG. 8, respectively.

Examples 35 to 39

Polymerization was carried out in the same way as in Example 34 except that the type of metal complex (A) and polymerization temperature were changed to those shown in Table 1.

Example 40

Addition copolymerization of norbornene and 2-acetoxymethyl-5-norbornene (precipitation polymerization)

After the inside of a three-neck flask equipped with a three-way stopcock and a mechanical stirrer was substituted with nitrogen, a solution of norbornene (9.42 g, 0.100 mol) dissolved in 5.4 ml of toluene, and 2-acetoxymethyl-5-norbornene prepared in Synthesis Example 1 (16.62 g, 0.100 mol) were added thereto, dissolved in ethyl acetate (70 ml) and heated to 80° C. After adding a catalyst solution of (π-allyl){2-[N-(2,6-diisopropylphenyl)iminomethyl]phenolate}palladium (Complex A-1) (4.3 mg, 0.010 mmol) synthesized in Example 1, triisopropyl phosphine [P(i-C$_3$H$_7$)$_3$] (manufactured by Strem Chemicals, Inc.; 1.6 mg, 0.010 mmol) and N,N-dimethylaniliumtetrakis(pentafluorophenyl)borate [(C$_6$H$_5$)(CH$_3$)$_2$NH][B(C$_6$F$_5$)$_4$] (manufactured by Strem Chemicals, Inc.; 8.0 mg, 0.010 mmol) dissolved in 3.5 ml of toluene, polymerization reaction was carried out at 80° C. for one hour. During the polymerization, polymer was precipitated in white powder form. After the reaction was completed, 8 ml of methanol added with small quantity of hydrochloric acid was added to the reaction solution to thereby terminate the reaction. The precipitated polymer was separated by filtration followed by washing, and then dried at 90° C. under reduced pressure for five hours to obtain 12.41 g of polymer in the white powder form. The catalytic activity calculated based on the polymer yield and the charge of the catalyst was 1241 g of polymer/mmol of palladium (Pd).

The obtained polymer was easily dissolved in a general solvent such as THF and chloroform and had a number average molecular weight (Mn) of 287,000 and a molecular distribution (Mw/Mn) of 2.18. The composition ratio of the 2-acetoxymethyl-5-norbornene monomer unit in the polymer calculated by the integral value of the $^1$H-NMR spectrum was 20.1 mol %.

Example 41

Addition copolymerization of norbornene and 2-acetoxymethyl-5-norbornene (precipitation polymerization)

Polymerization was carried out in the same way as in Example 40 except that the polymerization temperature and reaction time were changed to those shown in Table 1.

Example 42

Addition copolymerization of norbornene and 2-acetoxymethyl-5-norbornene (precipitation polymerization)

Polymerization was carried out in the same way as in Example 40 except that the polymerization solvent was changed from ethyl acetate to n-propyl acetate.

Example 43

Addition copolymerization of norbornene and 2-acetoxymethyl-5-norbornene (precipitation polymerization)

After the inside of a three-neck flask equipped with a three-way stopcock, a dripping funnel and a mechanical stirrer was substituted with nitrogen, a solution of norbornene (6.31 g, 0.067 mol) dissolved in 7.3 ml of toluene, and 2-acetoxymethyl-5-norbornene prepared in Synthesis Example 1 (22.11 g, 0.133 mol) were added thereto, dissolved in ethyl acetate (80 ml) and heated to 80° C. Separately, norbornene (16.29 g, 0.173 mol) dissolved in 19.0 ml of toluene, 2-acetoxymethyl-5-norbornene prepared in Synthesis Example 1 (14.46 g, 0.087 mol) and ethyl acetate were added to the dripping funnel. Subsequently, after adding to the flask a catalyst solution of (π-allyl){2-[N-(2,6-diisopropylphenyl)iminomethyl]phenolate}palladium (Complex A-1) (4.3 mg, 0.010 mmol) synthesized in Example 1, triisopropyl phosphine [P(i-C$_3$H$_7$)$_3$] (manufactured by Strem Chemicals, Inc.; 1.6 mg, 0.010 mmol) and N,N-dimethylaniliumtetrakis(pentafluorophenyl)borate [(C$_6$H$_5$)(CH$_3$)$_2$NH][B(C$_6$F$_5$)$_4$] (manufactured by Strem Chemicals, Inc.; 8.0 mg, 0.010 mmol) dissolved in 2.5 ml of toluene, thereby initiating polymerization. During the polymerization, polymer was precipitated in the form of white powder. After 30 minutes from the beginning of the polymerization, the instillation of the mixed solution charged in the dripping funnel was started and completed in 80 minutes while polymerization reaction was performed at 80° C. After the instillation was completed, polymerization reaction was performed at 80° C. for another 10 minutes. After two hours from the beginning of the polymerization, 8 ml of methanol added with small quantity of hydrochloric acid was added to the reaction solution to thereby terminate the reaction. The precipitated polymer was separated by filtration followed by washing, and then dried at 90° C. under reduced pressure for five hours to obtain 36.10 g of polymer in the white powder form. The catalytic activity calculated based on the polymer yield and the charge of the catalyst was 3610 g of polymer/mmol of palladium (Pd).

The obtained polymer was easily dissolved in a general solvent such as THF and chloroform and had a number average molecular weight (Mn) of 420,800 and a molecular distribution (Mw/Mn) of 2.77. The composition ratio of the 2-acetoxymethyl-5-norbornene monomer unit in the polymer calculated by the integral value of the $^1$H-NMR spectrum was 39.0 mol %.

Example 44

Addition copolymerization of norbornene and 2-acetoxymethyl-5-norbornene (precipitation polymerization)

Polymerization was carried out in the same way as in Example 43 except that a mixed solution of norbornene (27.12 g, 0.288 mol) dissolved in 31.0 ml of toluene, 2-acetoxymethyl-5-norbornene prepared in Synthesis Example 1 (23.94 g, 0.144 mol) and ethyl acetate (135 ml) charged in the dripping funnel was delivered by drops for 140 minutes and after the instillation was completed, polymerization reaction was further performed at 80° C. for 10 minutes, making the reaction time three hours in total. 54.00 g of polymer in the form of white powder was obtained. The catalytic activity calculated based on the polymer yield and the charge of the catalyst was 5400 g of polymer/mmol of palladium (Pd).

The obtained polymer was easily dissolved in a general solvent such as THF and chloroform and had a number average molecular weight (Mn) of 402,800 and a molecular distribution (Mw/Mn) of 3.22. The composition ratio of the 2-acetoxymethyl-5-norbornene monomer unit in the polymer calculated by the integral value of the $^1$H-NMR spectrum was 34.1 mol %.

Example 45

Addition copolymerization of norbornene and 2-acetoxymethyl-5-norbornene (precipitation polymerization)

Polymerization was carried out in the same way as in Example 43 except that a mixed solution of norbornene (38.04 g, 0.404 mol) dissolved in 44.0 ml of toluene, 2-acetoxymethyl-5-norbornene prepared in Synthesis Example 1 (33.58 g, 0.202 mol) and ethyl acetate (190 ml) charged in the dripping funnel was delivered by drops for 200 minutes and after the instillation was completed, polymerization reaction was further performed at 80° C. for 10 minutes, making the reaction time four hours in total. 68.10 g of polymer in the form of white powder was obtained. The catalytic activity calculated based on the polymer yield and the charge of the catalyst was 6810 g of polymer/mmol of palladium (Pd).

The obtained polymer was easily dissolved in a general solvent such as THF and chloroform and had a number average molecular weight (Mn) of 332,300 and a molecular distribution (Mw/Mn) of 3.33. The composition ratio of the 2-acetoxymethyl-5-norbornene monomer unit in the polymer calculated by the integral value of the $^1$H-NMR spectrum was 38.9 mol %.

Example 46

Addition copolymerization of norbornene and 2-acetoxymethyl-5-norbornene (polymerization using an n-hexane solvent)

After the inside of a three-neck flask equipped with a three-way stopcock and a mechanical stirrer was substituted with nitrogen, a solution of norbornene (manufactured by Tokyo Chemical Industries Co., Ltd.; 4.71 g, 0.050 mol) and 2-acetoxymethyl-5-norbornene prepared in Synthesis Example 1 (16.62 g, 0.100 mol) were added thereto and dissolved in 100 ml of n-hexane. After further adding a solution of N,N-dimethylaniliniumtetrakis(pentafluorophenyl)borate $[(C_6H_5)(CH_3)_2NH][B(C_6F_5)_4]$ (manufactured by Strem Chemicals, Inc.; 8.0 mg, 0.010 mmol) dissolved in 1 ml of dichloromethane, the resultant solution was heated to 90° C. After adding thereto a catalyst solution of (π-allyl){2-[N-(2,6-diisopropylphenyl)iminomethyl]phenolate}palladium (Complex A-1) (4.3 mg, 0.010 mmol) synthesized in Example 1 and prepared in another flask and triisopropyl phosphine $[P(i-C_3H_7)_3]$ (manufactured by Strem Chemicals, Inc.; 1.6 mg, 0.010 mmol) dissolved in 3.5 ml of toluene, polymerization reaction was carried out at 90° C. for 30 minutes. Although the polymer was precipitated in the form of white solid immediately after the beginning of the polymerization, the precipitate adhered to the inner wall of the flask due to the stickiness of the solid surface. Subsequently, a solution of norbornene (manufactured by Tokyo Chemical Industries Co., Ltd.; 4.71 g, 0.050 mol) as prepared separately dissolved in 5.4 ml of toluene was added to the reaction solution and polymerization reaction was further performed at 90° C. for 30 minutes. At this point, the polymer became sticky clumps, which were entangled with the stirring vanes. After the reaction was completed, 8 ml of methanol added with small quantity of hydrochloric acid was added to the reaction solution to thereby terminate the reaction. The polymer was dissolved by adding toluene and the solution was put in large quantity of methanol to thereby precipitate the polymer. The precipitated polymer was separated by filtration followed by washing, and then dried at 90° C. under reduced pressure for five hours to obtain 12.10 g of polymer in the white powder form. The catalytic activity calculated based on the polymer yield and the charge of the catalyst was 1210 g of polymer/mmol of palladium (Pd).

The obtained polymer was easily dissolved in a general solvent such as THF and chloroform and had a number average molecular weight (Mn) of 214,000 and a molecular distribution (Mw/Mn) of 2.46. The composition ratio of the 2-acetoxymethyl-5-norbornene monomer unit in the polymer calculated by the integral value of the $^1$H-NMR spectrum was 24.3 mol %.

Comparative Example 1

Addition copolymerization of norbornene and 2-acetoxymethyl-5-norbornene (polymerization according to the method of JP-A-2008-31304)

After the inside of a two-neck flask equipped with a three-way stopcock was substituted with nitrogen, 2-acetoxymethyl-5-norbornene prepared in Synthesis Example 1 (14.13 g, 0.085 mol) was added thereto and dissolved in 50 ml of toluene. After further adding thereto a solution of allylpalladiumchloridedimer $[[(C_3H_5)PdCl]_2]$ (manufactured by Wako Pure Chemical Industries Co., Ltd., 9 mg, 0.025 mmol) dissolved in 1 ml of toluene, a solution of tricyclohexylphosphine $[P(C_6H_{11})_3]$ (manufactured by Strem Chemicals Inc.; 14 mg, 0.050 mmol) dissolved in 1 ml of toluene and a solution of N,N-dimethylaniliniumtetrakis(pentafluorophenyl)borate $[(C_6H_5)(CH_3)_2NH][B(C_6F_5)_4]$ (manufactured by Strem Chemicals Inc., 60 mg, 0.075 mmol) dissolved in 1 ml of dichloromethane separately in that order, the flask was dipped in an oil bath and heated to 90° C. while being stirred. A solution of norbornene (manufactured by Tokyo Chemical Industries Co., Ltd.; 8.00 g, 0.085 mol) as prepared separately dissolved in 10 ml of toluene was added to the flask to thereby initiate polymerization reaction, and polymerization reaction was performed at 90° C. for two hours. After the reaction was completed, the reaction solution was put into large quantity of methanol to thereby precipitate polymers. The precipitated polymer was separated by filtration followed by washing, and then dried at 60° C. under reduced pressure for five hours to obtain 19.4 g of polymer in the white powder form. The catalytic activity calculated based on the polymer yield and the charge of the catalyst was 388 g of polymer/mmol of palladium (Pd).

The obtained polymer was easily dissolved in a general solvent such as THF and chloroform and had a number average molecular weight (Mn) of 58,000 and a molecular distribution (Mw/Mn) of 2.06. The composition ratio of the 2-acetoxymethyl-5-norbornene monomer unit in the polymer calculated by the integral value of the $^1$H-NMR spectrum was 37.3 mol %.

Comparative Example 2

Addition copolymerization of norbornene and 2-acetoxymethyl-5-norbornene (polymerization according to the method of JP-A-2008-31304)

Polymerization was carried out in the same way as in Comparative Example 1 except that allylpalladiumchloridedimer $[[(C_3H_5)PdCl]_2]$ (4.5 mg, 0.125 mmol), tricyclohexylphosphine $[P(C_6H_{11})_3]$ (7 mg, 0.025 mmol) and N,N-dimethylaniliniumtetrakis(pentafluorophenyl)borate $[(C_6H_5)(CH_3)_2NH][B(C_6F_5)_4]$ (30 mg, 0.0375 mmol) were used as a catalyst and the reaction was performed at 60° C. to obtain 4.3 g of polymer in the white powder form. The catalytic activity calculated based on the polymer yield and the charge of the catalyst was 172 g of polymer/mmol of palladium (Pd).

The obtained polymer was easily dissolved in a general solvent such as THF and chloroform and had a number average molecular weight (Mn) of 105,400 and a molecular distribution (Mw/Mn) of 1.98. The composition ratio of the 2-acetoxymethyl-5-norbornene monomer unit in the polymer calculated by the integral value of the $^1$H-NMR spectrum was 18.2 mol %.

Comparative Example 3

Addition homopolymerization of 2-acetoxymethyl-5-norbornene (polymerization according to the method of JP-A-2008-31304)

After the inside of a two-neck flask equipped with a three-way stopcock was substituted with nitrogen, 2-acetoxymethyl-5-norbornene prepared in Synthesis Example 1 (14.13 g, 0.085 mol) was added thereto and dissolved in 67 ml of toluene. After further adding thereto a solution of allylpalladiumchloridedimer (manufactured by Wako Pure Chemical Industries Co., Ltd., 4.5 mg, 0.0125 mmol) dissolved in 1 ml of toluene, a solution of tricyclohexylphosphine [$P(C_6H_{11})_3$] (manufactured by Strem Chemicals Inc.; 7 mg, 0.025 mmol) dissolved in 1 ml of toluene and a solution of N,N-dimethylaniliniumtetrakis(pentafluorophenyl)borate [$(C_6H_5)(CH_3)_2NH$][$B(C_6F_5)_4$] (manufactured by Strem Chemicals Inc., 30 mg, 0.0375 mmol) dissolved in 1 ml of dichloromethane separately in that order, the flask was dipped in an oil bath and heated to 90° C. while stirring to thereby carry out polymerization reaction for two hours. After the reaction was completed, the reaction solution was put into large quantity of methanol to thereby precipitate polymers. The precipitated polymer was separated by filtration followed by washing, and then dried at 60° C. under reduced pressure for five hours to obtain 0.35 g of polymer in the white powder form. The catalytic activity calculated based on the polymer yield and the charge of the catalyst was 14 g of polymer/mmol of palladium (Pd).

The obtained polymer was easily dissolved in a general solvent such as THF and chloroform and had a number average molecular weight (Mn) of 26,000 and a molecular distribution (Mw/Mn) of 1.86.

Comparative Example 4

Addition homopolymerization of 2-acetoxymethyl-5-norbornene (polymerization according to the method of "J. Organomet. Chem., 2009, 694, p. 297-303")

"J. Organomet. Chem., 2009, 694, p. 297-303" describes a method as follows. That is, as general reaction conditions, the document has description that "a solution of [(1,2,3-η)-1,1-diphenyl-2-methyl-2-propenyl]chloro[1,3-bis(2,6-diisopropylphenyl)-2-imidazolidene]palladium (1.6 mg, 0.0022 mmol) and lithium tetrakis(pentafluorophenyl)borate.diethyl ether complex, Li[$B(C_6F_5)_4$.2.5($C_2H_5$)$_2O$] (3.0 mg, 0.0034 mmol) dissolved in chlorobenzene (3 ml) was reacted under nitrogen atmosphere at room temperature for eight hours. Subsequently, the reaction solution was filtrated by a syringe filter, and the filtrate was added to a solution of 5-acetoxymethyl-2-norbornene (1.0 g, 6.6 mmol) dissolved in chlorobenzen (1 ml) as prepared separately. Next, the resultant solution was reacted at a predetermined temperature for 20 hours, and the powder obtained by reprecipitation in methanol (50 ml) was washed with methanol (20 ml) three times and further dried under vacuum". "J. Organomet. Chem., 2009, 694, p. 297-303" does not describe details on each of the production methods, but teaches in Table 3 that "in the case when setting the reaction time of one hour, charging [(1,2,3-η)-1,1-diphenyl-2-methyl-2-propenyl]chloro[1,3-bis(2,6-diisopropylphenyl)-2-imidazolidene]palladium in an amount of two thousandth of 5-acetoxymethyl-2-norbornene by molar ratio and lithium tetrakis(pentafluorophenyl)borate.diethyl ether complex, Li[$B(C_6F_5)_4$.2.5($C_2H_5$)$_2O$] in an amount of 1.5 times palladium complex by molar ratio, using chlorobenzene as a solvent and controlling the reaction temperature to 50° C., a polymer was obtained, in which a catalytic activity calculated based on the polymer yield and the charge of the catalyst was 123 g of polymer/mmol of palladium (Pd) and a number average molecular weight (Mn) was 65,000".

Comparative Example 5

Addition homopolymerization of 2-acetoxymethyl-5-norbornene (polymerization according to the method of "J. Organomet. Chem., 2009, 694, p. 297-303")

"J. Organomet. Chem., 2009, 694, p. 297-303" teaches in Table 3 that "in the case when setting the reaction time of four hours, charging [(1,2,3-η)-1,1-diphenyl-2-methyl-2-propenyl]chloro[1,3-bis(2,6-diisopropylphenyl)-2-imidazolidene] palladium in an amount of two thousandth of 5-acetoxymethyl-2-norbornene by molar ratio and lithium tetrakis (pentafluorophenyl)borate.diethyl ether complex, Li[$B(C_6F_5)_4$-$_{2.5}$($C_2H_5$)$_2O$] in an amount of 1.5 times palladium complex by molar ratio, using chlorobenzene as a solvent and controlling the reaction temperature to 50° C., a polymer was obtained, in which a catalytic activity calculated based on the polymer yield and the charge of the catalyst was 60 g of polymer/mmol of palladium (Pd) and a number average molecular weight (Mn) was 126,000".

Comparative Example 6

Addition copolymerization of 2-acetoxymethyl-5-norbornene using an Ni catalyst (precipitation polymerization)

After the inside of a 300 ml-volume three-neck flask equipped with a three-way stopcock and a mechanical stirrer was substituted with nitrogen, a solution of norbornene (manufactured by Tokyo Chemical Industries Co., Ltd.; 9.6 g, 0.102 mol) dissolved in 11.1 ml of toluene under nitrogen, 2-acetoxymethyl-5-norbornene (17.1 g, 0.103 mol) and 60 ml of ethyl acetate (manufactured by Showa Denko K.K.) were added to the flask. Meanwhile, bis(acetylacetonato)nickel (10.3 mg, 40 μmol), tris(pentafluorofenyl)boron [$B(C_6F_5)_3$] (61.0 mg, 120 μmol) and trimethylaluminum (manufactured by Sigma-Aldrich; 2.0 M toluene solution, 0.10 ml, 200 μmol) were charged in a 20 ml-volume glass ample under nitrogen and dissolved in 4 ml of anhydrous toluene, and the total solution was immediately added to the three-neck flask to thereby initiate polymerization. During the polymerization, the polymer was precipitated in the white powder form. Polymerization was performed at room temperature for 30 minutes and 8 ml of methanol added with small quantity of hydrochloric acid was added to the reaction solution to thereby terminate the reaction. The precipitated polymer was separated by filtration followed by washing, and then dried at 90° C. under reduced pressure for five hours to obtain 8.9 g of polymer in the white powder form. The catalytic activity calculated based on the polymer yield and the charge of the catalyst was 223 g of polymer/mmol of nickel (Ni).

The obtained polymer was easily dissolved in a general solvent such as THF and chloroform and had a number average molecular weight (Mn) of 687,000 and a molecular distribution (Mw/Mn) of 1.99. The composition ratio of the 2-acetoxymethyl-5-norbornene monomer unit in the polymer calculated by the integral value of the $^1H$-NMR spectrum was 26.0 mol %.

With respect to Examples 1 to 46 and Comparative Examples 1 to 6, type of the catalyst, polymerization conditions and the like are shown in Table 1 and the polymerization results are shown in Table 2. Each of the symbols in Table 1 has the meaning as follows:

Metal Complex (A):

A-1: (π-allyl){2-[N-(2,6-diisopropylphenyl)iminomethyl]phenolate}palladium
A-2: (π-allyl){2-[N-(2,6-diisopropylphenyl)iminomethyl]-4-fluorophenolate}palladium
A-3: (π-allyl)[2-(N-phenyliminomethyl)phenolate]palladium
A-4: (π-allyl){2-[N-(2,6-diisopropylphenyl)iminomethyl]-6-methylphenolate}palladium
A-5: allylpalladiumchloridedimer
A-6: [(1,2,3-η)-1,1-diphenyl-2-methyl-2-propenyl]chloro[1,3-bis(2,6-diisopropylphenyl)-2-imidazolidene]palladium
S-1: bis(acetylacetonato)nickel
Cocatalyst (B):
B-1: N,N-dimethylaniliniumtetrakis(pentafluorophenyl)borate,
B-2: trityltetrakis(pentafluorophenyl)borate,
B-3: lithiumtetrakis(pentafluorophenyl)borate,
B-4: tris(pentafluorophenyl)boron,
B-5: trimethylaluminum
Phosphine Ligand (C)
C-1: triisopropylphosphine,
C-2: tricyclohexylphosphine,
C-3: tri-t-butylphosphine
Monomer:
NB: norbornene,
ANB: 2-acetoxymethyl-5-norbornene All the polymers obtained in Examples 5 to 46 and Comparative Examples 1 to 3 and 6 were easily dissolved in a general solvent such as THF and chloroform.

TABLE 1

| | catalyst | | | | | | charge of monomer | | | | Polymerization conditions | |
| | metal complex | | cocatalyst | | phosphine ligand (C) | | charge of monomer | | additional charge of monomer | | polymerization temperature | Polylmerization time |
| | type | [mg] | type | [mg] | type | [mg] | NB [g] | ANB [g] | NB [g] | ANB [g] | [° C.] | [min] |
|---|---|---|---|---|---|---|---|---|---|---|---|---|
| Example 5 | A-1 | 4.3 | B-1 | 8.0 | C-1 | 1.6 | 4.71 | 16.62 | 4.71 × 1 | — | 70 | 30 × 2 = 60 |
| Example 6 | ↑ | ↑ | ↑ | ↑ | ↑ | ↑ | ↑ | ↑ | ↑ × 1 | — | 80 | 30 × 2 = 60 |
| Example 7 | ↑ | ↑ | ↑ | ↑ | ↑ | ↑ | ↑ | ↑ | ↑ × 1 | — | 90 | 30 × 2 = 60 |
| Example 8 | ↑ | ↑ | B-2 | 9.2 | ↑ | ↑ | ↑ | ↑ | ↑ × 1 | — | 80 | 30 × 2 = 60 |
| Example 9 | ↑ | ↑ | B-1 | 8.0 | C-2 | 2.8 | ↑ | ↑ | ↑ × 1 | — | ↑ | 30 × 2 = 60 |
| Example 10 | ↑ | ↑ | ↑ | ↑ | C-3 | 2.0 | ↑ | ↑ | ↑ × 1 | — | ↑ | 30 × 2 = 60 |
| Example 11 | ↑ | ↑ | ↑ | ↑ | C-1 | 1.6 | ↑ | ↑ | ↑ × 5 | 5.0 × 2 | ↑ | 30 × 6 = 180 |
| Example 12 | ↑ | ↑ | ↑ | ↑ | ↑ | ↑ | ↑ | ↑ | ↑ × 5 | ↑ × 2 | 70 | 30 × 6 = 180 |
| Example 13 | ↑ | ↑ | ↑ | ↑ | ↑ | 2.4 | ↑ | ↑ | ↑ × 5 | ↑ × 2 | ↑ | 30 × 6 = 180 |
| Example 14 | ↑ | 6.4 | ↑ | 18.0 | ↑ | 3.6 | ↑ | ↑ | ↑ × 5 | ↑ × 2 | ↑ | 30 × 6 = 180 |
| Example 15 | ↑ | 4.3 | ↑ | 8.0 | ↑ | 1.6 | ↑ | ↑ | ↑ × 1 | — | 80 | 30 × 2 = 60 |
| Example 16 | A-2 | 4.5 | ↑ | ↑ | ↑ | ↑ | ↑ | ↑ | ↑ × 1 | — | 60 | 30 × 2 = 60 |
| Example 17 | ↑ | ↑ | ↑ | ↑ | ↑ | ↑ | ↑ | ↑ | ↑ × 1 | — | 70 | 30 × 2 = 60 |
| Example 18 | ↑ | ↑ | ↑ | ↑ | ↑ | ↑ | ↑ | ↑ | ↑ × 1 | — | 80 | 30 × 2 = 60 |
| Example 19 | ↑ | ↑ | ↑ | ↑ | ↑ | ↑ | ↑ | ↑ | ↑ × 1 | — | 90 | 30 × 2 = 60 |
| Example 20 | ↑ | ↑ | B-2 | 9.2 | ↑ | ↑ | ↑ | ↑ | ↑ × 1 | — | 80 | 30 × 2 = 60 |
| Example 21 | ↑ | ↑ | B-1 | 8.0 | ↑ | ↑ | 7.06 | 24.93 | 7.06 × 1 | — | 70 | 30 × 2 = 60 |
| Example 22 | ↑ | ↑ | ↑ | ↑ | ↑ | ↑ | ↑ | ↑ | ↑ × 1 | — | 80 | 30 × 2 = 60 |
| Example 23 | ↑ | ↑ | ↑ | ↑ | ↑ | ↑ | ↑ | ↑ | ↑ × 1 | — | 90 | 30 × 2 = 60 |
| Example 24 | A-3 | 3.4 | ↑ | ↑ | ↑ | ↑ | 4.71 | 16.62 | 4.71 × 1 | — | 80 | 30 × 2 = 60 |
| Example 25 | ↑ | ↑ | ↑ | ↑ | ↑ | ↑ | ↑ | ↑ | ↑ × 1 | — | 90 | 30 × 2 = 60 |
| Example 26 | ↑ | ↑ | ↑ | ↑ | ↑ | ↑ | 7.06 | 24.93 | 7.06 × 1 | — | 70 | 30 × 2 = 60 |
| Example 27 | ↑ | ↑ | ↑ | ↑ | ↑ | ↑ | ↑ | ↑ | ↑ × 1 | — | 80 | 30 × 2 = 60 |
| Example 28 | ↑ | ↑ | ↑ | ↑ | ↑ | ↑ | ↑ | ↑ | ↑ × 1 | — | 90 | 30 × 2 = 60 |
| Example 29 | ↑ | ↑ | ↑ | ↑ | ↑ | ↑ | ↑ | ↑ | ↑ × 1 | — | 80 | 15 × 2 = 30 |
| Example 30 | A-4 | 4.4 | ↑ | ↑ | ↑ | ↑ | ↑ | ↑ | ↑ × 1 | — | 70 | 30 × 2 = 60 |
| Example 31 | ↑ | ↑ | ↑ | ↑ | ↑ | ↑ | ↑ | ↑ | ↑ × 1 | — | 80 | 30 × 2 = 60 |
| Example 32 | ↑ | ↑ | ↑ | ↑ | ↑ | ↑ | ↑ | ↑ | ↑ × 1 | — | 90 | 30 × 2 = 60 |
| Example 33 | ↑ | ↑ | ↑ | ↑ | ↑ | ↑ | ↑ | ↑ | ↑ × 1 | — | 80 | 15 × 2 = 30 |
| Example 34 | A-1 | 4.3 | ↑ | ↑ | ↑ | ↑ | — | 16.62 | — | — | 80 | 60 × 1 = 60 |
| Example 35 | A-3 | 3.4 | ↑ | ↑ | ↑ | ↑ | — | ↑ | — | — | 80 | 60 × 1 = 60 |
| Example 36 | ↑ | ↑ | ↑ | ↑ | ↑ | ↑ | — | ↑ | — | — | 90 | 60 × 1 = 60 |
| Example 37 | A-4 | 4.4 | ↑ | ↑ | ↑ | ↑ | — | ↑ | — | — | 70 | 60 × 1 = 60 |
| Example 38 | ↑ | ↑ | ↑ | ↑ | ↑ | ↑ | — | ↑ | — | — | 80 | 60 × 1 = 60 |
| Example 39 | ↑ | ↑ | ↑ | ↑ | ↑ | ↑ | — | ↑ | — | — | 90 | 60 × 1 = 60 |
| Example 40 | A-1 | 4.3 | ↑ | ↑ | ↑ | ↑ | 9.42 | ↑ | — | — | 80 | 60 × 1 = 60 |
| Example 41 | ↑ | ↑ | ↑ | ↑ | ↑ | ↑ | ↑ | ↑ | — | — | 90 | 30 × 1 = 30 |
| Example 42 | ↑ | ↑ | ↑ | ↑ | ↑ | ↑ | ↑ | ↑ | — | — | 80 | 60 × 1 = 60 |
| Example 43 | ↑ | ↑ | ↑ | ↑ | ↑ | ↑ | 6.31 | 22.11 | 16.29 × 1 | 14.46 × 1 | 80 | 30 + 80 + 10 = 120 |
| Example 44 | ↑ | ↑ | ↑ | ↑ | ↑ | ↑ | ↑ | ↑ | 27.12 × 1 | 23.94 × 1 | 80 | 30 + 140 + 10 = 180 |
| Example 45 | ↑ | ↑ | ↑ | ↑ | ↑ | ↑ | ↑ | ↑ | 38.04 × 1 | 33.58 × 1 | 80 | 30 + 200 + 10 = 240 |
| Example 46 | ↑ | ↑ | ↑ | ↑ | ↑ | ↑ | 4.71 | 16.62 | 4.71 × 1 | — | 90 | 30 × 2 = 60 |
| Comp. Ex. 1 | A-5 | 9 | ↑ | 60.0 | C-2 | 14.0 | 8 | 14.13 | — | — | 90 | 120 × 1 = 120 |
| Comp. Ex. 2 | ↑ | 4.5 | ↑ | 30.0 | ↑ | 7.0 | ↑ | ↑ | — | — | 60 | 120 × 1 = 120 |
| Comp. Ex. 3 | ↑ | ↑ | ↑ | ↑ | ↑ | ↑ | ↑ | ↑ | — | — | 90 | 120 × 1 = 120 |
| Comp. Ex. 4 | A-6 | — | B-3 | — | — | — | — | — | — | — | 50 | 60 × 1 = 60 |
| Comp. Ex. 5 | ↑ | — | ↑ | — | — | — | — | — | — | — | 50 | 240 × 1 = 240 |
| Comp. Ex. 6 | S-1 | 10.3 | B-4 / B-5 | 61.0 / 14.4 | — | — | 9.60 | 17.10 | — | — | Room temperature | 30 × 1 = 30 |

TABLE 2

| | Polymerization results | | | | | |
|---|---|---|---|---|---|---|
| | polymer yield [g] | catalytic activity [g/mmol] | Molecular weight | | | ANB content [mol %] |
| | | | Mn | Mw | Mw/Mn | |
| Example 5 | 10.52 | 1052 | 916,000 | 1,940,000 | 2.12 | 20.4 |
| Example 6 | 13.09 | 1309 | 478,000 | 1,310,000 | 2.75 | 24.1 |
| Example 7 | 12.98 | 1298 | 207,000 | 540,000 | 2.61 | 24.8 |
| Example 8 | 11.53 | 1153 | 397,000 | 970,000 | 2.45 | 22.2 |
| Example 9 | 1.83 | 183 | 706,000 | 1,330,000 | 1.88 | 16.6 |
| Example 10* | 0.83 | 83 | 283,400 | 884,200 | 3.12 | 26.9 |
| Example 11 | 33.90 | 3390 | 283,400 | 880,000 | 3.12 | 19.3 |
| Example 12 | 28.84 | 2884 | 892,000 | 2,170,000 | 2.43 | 16.9 |
| Example 13 | 37.19 | 3719 | 634,000 | 1,680,000 | 2.65 | 19.0 |
| Example 14 | 54.50 | 3633 | 617,000 | 2,000,000 | 3.24 | 17.6 |
| Example 15 | 4.30 | 430 | 355,000 | 1,010,000 | 2.84 | 17.9 |
| Example 16 | 13.58 | 1358 | 817,000 | 1,690,000 | 2.07 | 31.2 |
| Example 17 | 15.67 | 1567 | 462,000 | 1,040,000 | 2.26 | 32.1 |
| Example 18 | 16.27 | 1627 | 274,000 | 710,000 | 2.58 | 29.6 |
| Example 19 | 17.40 | 1740 | 211,000 | 510,000 | 2.41 | 31.0 |
| Example 20 | 16.38 | 1638 | 266,000 | 640,000 | 2.41 | 29.2 |
| Example 21 | 20.31 | 2031 | 734,000 | 1,700,000 | 2.32 | 26.4 |
| Example 22 | 23.46 | 2346 | 462,000 | 1,110,000 | 2.40 | 29.0 |
| Example 23 | 25.62 | 2562 | 300,000 | 770,000 | 2.57 | 30.4 |
| Example 24 | 17.62 | 1762 | 460,000 | 1,050,000 | 2.28 | 27.6 |
| Example 25 | 19.77 | 1977 | 244,000 | 600,000 | 2.45 | 27.6 |
| Example 26 | 22.93 | 2293 | 660,000 | 1,600,000 | 2.43 | 25.0 |
| Example 27 | 24.89 | 2489 | 370,000 | 930,000 | 2.52 | 28.6 |
| Example 28 | 25.34 | 2534 | 321,000 | 830,000 | 2.60 | 30.6 |
| Example 29 | 21.51 | 2151 | 428,000 | 1,040,000 | 2.44 | 25.0 |
| Example 30 | 19.02 | 1902 | 720,000 | 1,580,000 | 2.20 | 25.4 |
| Example 31 | 23.68 | 2368 | 297,000 | 750,000 | 2.53 | 30.4 |
| Example 32 | 23.61 | 2361 | 179,000 | 460,000 | 2.56 | 30.0 |
| Example 33 | 20.11 | 2011 | 489,000 | 1,120,000 | 2.30 | 27.0 |
| Example 34 | 6.59 | 659 | 208,000 | 430,000 | 2.05 | 100.0 |
| Example 35 | 4.56 | 456 | 249,000 | 440,000 | 1.78 | 100.0 |
| Example 36 | 6.06 | 606 | 180,000 | 400,000 | 2.22 | 100.0 |
| Example 37 | 5.03 | 503 | 271,000 | 510,000 | 1.87 | 100.0 |
| Example 38 | 6.76 | 676 | 330,000 | 600,000 | 1.82 | 100.0 |
| Example 39 | 9.57 | 957 | 194,000 | 420,000 | 2.19 | 100.0 |
| Example 40 | 12.41 | 1241 | 287,000 | 626,000 | 2.18 | 20.1 |
| Example 41 | 10.99 | 1099 | 197,000 | 429,000 | 2.18 | 24.6 |
| Example 42 | 9.78 | 978 | 252,000 | 552,000 | 2.19 | 22.3 |
| Example 43 | 36.10 | 3610 | 420,800 | 1,166,400 | 2.77 | 39.0 |
| Example 44 | 54.00 | 5400 | 402,800 | 1,295,400 | 3.22 | 34.1 |
| Example 45 | 68.10 | 6810 | 332,300 | 1,106,300 | 3.33 | 38.9 |
| Example 46 | 12.10 | 1210 | 214,000 | 526,400 | 2.46 | 24.3 |
| Comparative Ex. 1 | 19.40 | 388 | 58,000 | 120,000 | 2.06 | 37.3 |
| Comparative Ex. 2 | 4.30 | 172 | 105,400 | 210,000 | 1.98 | 18.2 |
| Comparative Ex. 3 | 0.35 | 14 | 26,000 | 50,000 | 1.86 | 100.0 |
| Comparative Ex. 4 | — | 123 | 65,000 | 134,000 | 2.05 | 100.0 |
| Comparative Ex. 5 | — | 60 | 126,000 | 199,000 | 1.57 | 100.0 |
| Comparative Ex. 6 | 8.90 | 223 | 687,000 | 1,367,000 | 1.99 | 26.0 |

*The molecular weight distribution in Example 10 has two peaks; values such as Mn is an overall average.

Regarding copolymerization of norbornene and 2-acetoxymethyl-5-norbornene, a copolymer having a molecular weight (Mn) exceeding 200,000 has not been produced by the method of JP-A-2008-31304, and the catalytic activity having prospect of industrially practical use was not confirmed (Comparative Examples 1 to 2). With the nickel (Ni) catalyst system in Comparative Example 6, a copolymer having a high molecular weight was obtained but the method was not sufficient in terms of the catalytic activity. According to the production method of the embodiment of the present invention, norbornene copolymers having excellent mechanical properties and molecular weight (Mn) exceeding 200,000 was obtained with the catalytic activity having prospect of industrially practical use (Examples 1 to 33, 40 to 46).

On the other hand, regarding homopolymerization of 2-acetoxymethyl-5-norbornene monomers, a homopolymer having a molecular weight (Mn) exceeding 200,000 has not been produced by the method of "J. Organomet. Chem., 2009, 694, p. 297-303", and the catalytic activity having prospect of industrially practical use was not confirmed even in the case of homopolymer having molecular weight (Mn) less than 200,000 (Comparative Examples 3). According to the method for producing homopolymer of norbornene of the embodiment of the present invention, polymers having excellent mechanical properties and molecular weight (Mn) exceeding 100,000 was obtained with the catalytic activity having prospect of industrially practical use (Examples 34 to 39).

The norbornene (co)polymer obtained by the production method of the embodiment of the present invention has excellent properties such as transparency, heat resistance, low water absorption and electric insulating property, and can be used for optical molded products such as lenses and polarizing films; films, carrier tapes, film capacitors, electric insulating materials for flexible printed circuit boards and the like; and medical containers such as press-through packages, infusion bags and chemical vials; food-packaging molded product such as plastic wraps and trays; casings for electric appliances; automobile interior parts such as an inner panel; building materials for a carport, glazing and the like; etc.

Obviously, numerous modifications and variations of the present invention are possible in light of the above teachings. It is therefore to be understood that within the scope of the appended claims, the invention may be practiced otherwise than as specifically described herein.

The invention claimed is:

1. A catalyst for a polymerization of norbornene monomers, the catalyst comprising:
a transition metal complex represented by a formula (1);
a cocatalyst to generate a cationic transition metal compound by reacting with the transition metal complex, the cocatalyst being an ionic compound; and
a phosphine ligand,

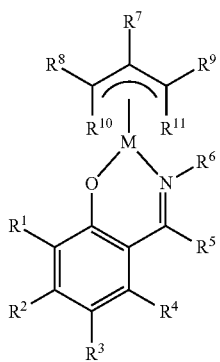

(1)

wherein
M represents one transition metal belonging to Group 8, Group 9 or Group 10 of the Periodic Table of the Elements issued in 1991,
each of $R^1$, $R^2$, $R^3$ and $R^4$ independently represents a hydrogen atom, a substituted or unsubstituted hydrocarbon group having 1 to 20 carbon atoms, a halogen atom, an alkoxy group, an aryloxy group, a silyl group having 1 to 20 carbon atoms, a siloxy group containing a hydrocarbon group having 1 to 20 carbon atoms, a nitro group, a cyano group, an amide group containing a hydrocarbon group having 1 to 10 carbon atoms or a dialkylamino group containing an alkyl group having 1 to 10 carbon atoms, or
each of $R^1$, $R^2$, $R^3$ and $R^4$ independently represents a hydrogen atom, a substituted or unsubstituted hydrocarbon group having 1 to 20 carbon atoms, a halogen atom, an alkoxy group, an aryloxy group, a silyl group having 1 to 20 carbon atoms, a siloxy group containing a hydrocarbon group having 1 to 20 carbon atoms, a nitro group, a cyano group, an amide group containing a hydrocarbon group having 1 to 10 carbon atoms or dialkylamino group containing an alkyl group having 1 to 10 carbon atoms, and at least two of $R^1$, $R^2$, $R^3$ and $R^4$ bond to each other to form a ring structure,
$R^5$ represents a hydrogen atom or a hydrocarbon group having 1 to 20 carbon atoms,
$R^6$ represents a hydrocarbon group having 1 to 20 carbon atoms, and
each of $R^7$, $R^8$, $R^9$, $R^{10}$ and $R^{11}$ independently represents a hydrogen atom, a halogen atom or a hydrocarbon group having 1 to 20 carbon atoms, or each of $R^7$, $R^8$, $R^9$, $R^{10}$ and $R^{11}$ independently represents a hydrogen atom, a halogen atom or a hydrocarbon group having 1 to 20 carbon atoms, and at least two of $R^7$, $R^8$, $R^9$, $R^{10}$ and $R^{11}$ bond to each other to form a ring structure.

2. The catalyst as claimed in claim 1, wherein M represents palladium (Pd) or nickel (Ni), $R^5$ represents a hydrogen atom, $R^6$ represents a substituted or unsubstituted phenyl group, and each of $R^7$, $R^8$, $R^9$, $R^{10}$ and $R^{11}$ represents a hydrogen atom.

3. The catalyst as claimed in claim 2, wherein M represents palladium, $R^1$ represents a hydrogen atom or a methyl group, each of $R^2$ and $R^4$ represents a hydrogen atom, $R^3$ represents a hydrogen atom or a fluorine atom, and $R^6$ represents a phenyl group or a 2,6-diisopropylphenyl group.

4. The catalyst as claimed in claim 1, wherein the cocatalyst is trityltetrakis(pentafluorophenyl)borate or N,N-dimethylaniliniumtetrakis(pentafluorophenyl)borate.

5. The catalyst as claimed in claim 1, wherein the phosphine ligand is tricyclohexylphosphine, tri-t-butylphosphine or triisopropylphosphine.

6. A method for producing a norbornene polymer comprising:
homopolymerizing norbornene monomers in a presence of the catalyst as claimed in claim 1.

7. A method for producing a norbornene copolymer comprising:
copolymerizing norbornene monomers in a presence of the catalyst as claimed in claim 1.

8. A method for producing a norbornene copolymer comprising:
copolymerizing norbornene monomers and vinyl monomers in a presence of the catalyst as claimed in claim 1.

9. A method for producing a norbornene copolymer comprising:
copolymerizing first norbornene monomers corresponding to a first monomer unit represented by a formula (2) and second norbornene monomers corresponding to a second monomer unit represented by a formula (3) in a presence of the catalyst as claimed in claim 1 to form the norbornene copolymer including the first monomer unit and the second monomer unit,

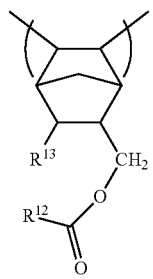

(2)

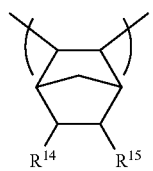

(3)

wherein $R^{12}$ represents an alkyl group having 1 to 10 carbon atoms, and each of $R^{13}$, $R^{14}$ and $R^{15}$ independently represents a hydrogen atom or an alkyl group having 1 to 10 carbon atoms.

10. The method as claimed in claim 9, wherein the norbornene copolymer essentially consists of the monomer unit represented by the formula (2) and the monomer unit represented by the formula (3).

* * * * *